US012290366B2

(12) United States Patent
Attari et al.

(10) Patent No.: US 12,290,366 B2
(45) Date of Patent: May 6, 2025

(54) UROFLOWMETRY SYSTEMS HAVING WEARABLE UROFLOWMETERS, AND METHODS OF OPERATING THE SAME

(71) Applicants: THE REGENTS OF THE UNIVERSITY OF MICHIGAN, Ann Arbor, MI (US); THE PROCTER & GAMBLE COMPANY, Cincinnati, OH (US)

(72) Inventors: Ali Attari, Ann Arbor, MI (US); James A. Ashton-Miller, Ann Arbor, MI (US); John O. Delancey, Ann Arbor, MI (US); Mark A. Burns, Ann Arbor, MI (US); Tana Marie Kirkbride, Cincinnati, OH (US); Edward Paul Carlin, Mason, OH (US); Alexzandra Joan Ramachandran, Blue Ash, OH (US); Carol A. Day, Cincinnati, OH (US)

(73) Assignees: THE REGENTS OF THE UNIVERSITY OF MICHIGAN, Ann Arbor, MI (US); THE PROCTER & GAMBLE COMPANY, Cincinnati, OH (US)

( * ) Notice: Subject to any disclaimer, the term of this patent is extended or adjusted under 35 U.S.C. 154(b) by 1188 days.

(21) Appl. No.: 17/078,999

(22) Filed: Oct. 23, 2020

(65) Prior Publication Data
US 2021/0121112 A1  Apr. 29, 2021

Related U.S. Application Data

(60) Provisional application No. 62/925,309, filed on Oct. 24, 2019.

(51) Int. Cl.
*A61B 5/20* (2006.01)
*A61B 10/00* (2006.01)
(Continued)

(52) U.S. Cl.
CPC .......... *A61B 5/208* (2013.01); *A61B 10/007* (2013.01); *G01G 17/04* (2013.01); *G01N 33/493* (2013.01)

(58) Field of Classification Search
CPC ......... A61B 5/208; A61B 10/007; G01P 5/12; A61F 5/455; A61F 5/451; A61F 5/453;
(Continued)

(56) References Cited

U.S. PATENT DOCUMENTS 3,352,154 A   11/1967  Djorup
3,460,123 A *  8/1969  Bass ............... A61F 13/42
                                              340/573.5
(Continued)

FOREIGN PATENT DOCUMENTS

CN    202589540 U    12/2012
FR    3015884 A1 *  7/2015  ........... A61F 5/4556
(Continued)

OTHER PUBLICATIONS

Herzog et al., "Two-year Incidence, Remission, and Change Patterns of Urinary Incontinence in Noninstitutionalized Older Adults", Journal of Gerontology: Medical Sciences, vol. 45, No. 2, 1990, M67-M74.
(Continued)

*Primary Examiner* — Benjamin S Melhus
(74) *Attorney, Agent, or Firm* — MARSHALL, GERSTEIN & BORUN LLP

(57) ABSTRACT

Wearable uroflowmetry systems having wearable uroflowmeters are disclosed. A disclosed example uroflowmetry system comprises a wearable uroflowmeter including: a funnel portion having an end configured to secure the funnel portion against a person, an outlet opposite the end, and a funnel configured to capture urine excreted by the person when the end is secured against the person, and to direct the
(Continued)

captured urine into the outlet; a fluid passage portion having an opening configured to receive the urine from the outlet of the funnel portion, and a fluid channel to pass the received urine along a length of the fluid passage portion; and a measuring portion having a sensor in the fluid channel configured to collect one or more measurements of the urine as the urine passes the sensor, the measurements representative of at least one of a property of the urine, or a flow characteristic of the urine.

19 Claims, 21 Drawing Sheets

(51) Int. Cl.
    *G01G 17/04* (2006.01)
    *G01N 33/493* (2006.01)
(58) Field of Classification Search
    CPC ........ A61F 5/4553; A61F 5/4556; A61F 5/44; G01N 33/493
    See application file for complete search history.

(56) References Cited

U.S. PATENT DOCUMENTS

| | | | |
|---|---|---|---|
| 3,575,050 A | 4/1971 | Lynnworth | |
| 3,592,195 A * | 7/1971 | Van Wagenen | A61F 5/451 340/384.1 |
| 4,187,722 A * | 2/1980 | Layton | G01F 1/06 600/584 |
| 4,246,901 A | 1/1981 | Frosch et al. | |
| 4,297,881 A | 11/1981 | Sasayama et al. | |
| 4,307,618 A | 12/1981 | James et al. | |
| 4,334,186 A | 6/1982 | Sasayama et al. | |
| 4,568,339 A | 2/1986 | Steer | |
| 5,002,541 A * | 3/1991 | Conkling | A61F 5/44 604/324 |
| 5,046,510 A | 9/1991 | Ams et al. | |
| 5,062,304 A | 11/1991 | Van Buskirk et al. | |
| 5,263,369 A * | 11/1993 | Cutler | G01F 1/6965 73/204.18 |
| 5,285,532 A * | 2/1994 | Sealy | A47K 11/12 4/144.1 |
| 5,735,835 A | 4/1998 | Holland | |
| 5,893,176 A | 4/1999 | Magiera et al. | |
| 6,021,531 A | 2/2000 | Kirko | |
| 6,931,943 B1 | 8/2005 | Aundal | |
| 7,357,035 B2 | 4/2008 | Liu et al. | |
| 7,691,092 B2 | 4/2010 | Corcos et al. | |
| 8,141,420 B2 | 3/2012 | Hirao | |
| 8,904,881 B2 | 12/2014 | Sonnenberg et al. | |
| 9,155,525 B2 | 10/2015 | Lipinsky et al. | |
| 9,400,197 B2 | 7/2016 | Najafi et al. | |
| 9,502,995 B2 | 11/2016 | Najafi et al. | |
| 10,316,503 B2 * | 6/2019 | Lu | A61G 9/00 |
| 2002/0193760 A1 * | 12/2002 | Thompson | A61F 5/4556 604/347 |
| 2005/0177070 A1 * | 8/2005 | Levinson | A61F 5/455 604/323 |
| 2007/0252713 A1 * | 11/2007 | Rondoni | A61B 5/6808 340/573.5 |
| 2007/0252714 A1 * | 11/2007 | Rondoni | A61N 1/36007 340/573.5 |
| 2007/0255176 A1 * | 11/2007 | Rondoni | A61B 5/202 600/573 |
| 2010/0137743 A1 * | 6/2010 | Nishtala | A61B 5/208 600/584 |
| 2010/0152684 A1 | 6/2010 | Kim et al. | |
| 2011/0046514 A1 * | 2/2011 | Greenwald | G01F 1/662 702/45 |
| 2011/0265576 A1 | 11/2011 | Cha et al. | |
| 2012/0078137 A1 * | 3/2012 | Mendels | G01F 23/2924 600/584 |
| 2012/0179387 A1 * | 7/2012 | Deng | G09B 23/303 702/19 |
| 2012/0226196 A1 * | 9/2012 | DiMino | A61B 5/208 600/584 |
| 2012/0302917 A1 * | 11/2012 | Fitzgerald | A61F 5/4404 600/575 |
| 2014/0276214 A1 | 9/2014 | Lipinsky et al. | |
| 2014/0283604 A1 | 9/2014 | Najafi et al. | |
| 2014/0296746 A1 | 10/2014 | Whitaker et al. | |
| 2015/0135423 A1 * | 5/2015 | Sharpe | A61F 5/455 4/471 |
| 2018/0021184 A1 * | 1/2018 | Monson | H01Q 9/0457 340/573.5 |
| 2020/0375781 A1 * | 12/2020 | Staali | A61M 1/71 |
| 2022/0354404 A1 * | 11/2022 | Van Batavia | A61B 5/486 |

FOREIGN PATENT DOCUMENTS

| | | | | |
|---|---|---|---|---|
| GB | 2191095 A | * | 12/1987 | ............ A61F 5/453 |
| WO | WO-2009/035599 A1 | | 3/2009 | |
| WO | WO-2013138537 A1 | * | 9/2013 | ........ A61M 5/16813 |
| WO | WO-2017/036952 A1 | | 3/2017 | |
| WO | WO-2018235065 A1 | * | 12/2018 | .......... A61F 5/4405 |

OTHER PUBLICATIONS

Thomas et al., "Prevalence of Urinary Incontinence", BMJ, vol. 281, 1980, pp. 1243-1245.
Sutherst et al., "Assessing the Severity of Urinary Incontinence in Women by Weighing Perineal Pads", The Lancet, May 23, 1981, pp. 1128-1130.
Miller et al., "Quantification of Cough-Related Urine Loss Using the Paper Towel Test", Obstetrics & Gynecology, vol. 91, No. 5, Part 1, May 1998, pp. 705-709.
Brubaker et al., "The External Urethral Barrier for Stress Incontinence: A Multicenter Trial of Safety and Efficacy", Obstetrics & Gynecology, vol. 93, No. 6, 1980, pp. 932-937.
Locher et al., "Reliability Assessment of the Bladder Diary for Urinary Incontinence in Older Women", Journal of Gerontology: Medical Sciences, vol. 56A, No. 1, 2001, M32-M35.
Mangera et al., "Development of Two Electronic Bladder Diaries: A Patient and Healthcare Professionals Pilot Study", Neurourology and Urodynamics, vol. 33, 2014, pp. 1101-1109.
Baik et al., "Highly Adaptable and Biocompatible Octopus-Like Adhesive Patches with Meniscus-Controlled Unfoldable 3D Microtips for Underwater Surface and Hairy Skin", Advanced Science, vol. 5, 2018, 7 pages.
Lin et al., "Low-Power Micro-fabricated Liquid Flow-rate Sensor", Anal. Methods, vol. 7, 2015, pp. 3981-3987.
Sadeghi et al., "Air Flow Sensing Using Micro-wire-bonded Hair-like Hot-wire Anemometry", J. Micromech. Microeng. 23, 2013, 12 pages.
Yaroshenko et al., "Determination of Urine Ionic Composition with Potentiometric Multisensor System", Talanta vol. 131, 2015, pp. 556-561.
Huang et al., "A Flexible pH Sensor Based on the Iridium Oxide Sensing Film", Sensors and Actuators A, vol. 169, 2011, 11 pages.
Yang et al., "Real-time Contaminant Detection and Classification in a Drinking Water Pipe Using Conventional Water Quality Sensors: Techniques and Experimental Results", Journal of Environmental Management, vol. 90, 2009, pp. 2494-2506.
Lin et al., "Multifunctional Water Sensors for pH, ORP, and Conductivity Using Only Microfabricated Platinum Electrodes", Sensors, vol. 17, No. 1655, 2017, 9 pages.
Turner et al., "The Electrical Conductivity of the Blood and Urine in Health and in Disease, and as a Test of the Functional Efficiency of the Kidney", Transactions, Medico-Chirurgical Society of Edinburgh, vol. 26, 1907, pp. 77-86.
Shinwari et al., "Microfabricated Reference Electrodes and Their Biosensing Applications", Sensors, vol. 10, 2010, pp. 1679-1715.
Oosterbroek et al., "A Micromachined Pressure/Flow-sensor", Sensors and Actuators, vol. 77, 1999, pp. 167-177.

(56) References Cited

OTHER PUBLICATIONS

Peezy Midstream USA, https://web.archive.org/weg/20181010194121/https:/forte-medical.co.uk/, Oct. 10, 2018, retrieved from the internet on Oct. 22, 2020, 3 pages.

* cited by examiner

UROFLOWMETRY SYSTEMS HAVING WEARABLE UROFLOWMETERS, AND METHODS OF OPERATING THE SAME

CROSS-REFERENCE TO RELATED APPLICATION

This application claims priority to and the benefit of U.S. Provisional Patent Application No. 62/925,309, filed Oct. 24, 2019, the entirety of which is hereby incorporated herein by reference.

GOVERNMENT LICENSE RIGHTS

This invention was made with government support under AG024824 and DK122379 awarded by the National Institutes of Health. The government has certain rights in the invention.

FIELD OF THE DISCLOSURE

This disclosure relates generally to uroflowmetry and, more particularly, to uroflowmetry systems having wearable uroflowmeters, and methods of operating the same.

BACKGROUND

Urinary incontinence is an important socioeconomic problem affecting between 8.5% and 38% of women and 3% and 11% of men. While clinical tools such as a commode-style uroflowmeter may be used to measure maximum urine flow rate and bladder emptying capacity as a baseline measurement of bladder storage and voiding, clinical tools are not suitable or applicable for measuring when and how much urine leaked during urinary incontinent episodes during daily activities (e.g., walking, stretching, lifting, sports, an unexpected sneeze, during times of urinary urgency, or unexpectedly), in a cognitively-impaired individual and/or in a person who is unresponsive.

Currently, regardless of the cause of a patient's urinary incontinence, the standard clinical measurement of urine leakage involves self-reporting of the frequency and subjective estimate of severity of urine leakage episodes via a urine voiding diary manually kept by the patient over 3 to 7 consecutive days of daily activities. However, the amount of urine leaked cannot be reliably estimated and because patients may be distracted at the time of a leakage episode, they may forget to enter the episode in the diary, the may enter inaccurate information, they may not be motivated to enter the episode, or they may not even feel or notice the episode because of distractions. Thus, a self-reporting voiding diary has limitations such as recall bias, especially in the case of older and/or cognitively-impaired individuals. In addition, voiding diaries cannot quantify urine leakage flow rate because no means is provided for the temporal recording of flow rate or amount. The quantification of both urine leakage flow rates and leakage volumes is important because large flow rates can exceed the ability of certain anti-incontinence products, such absorbent pads, to absorb the fluid fast enough, thereby causing the urine to flow beyond the pad to the lower limbs and even clothing, with humiliating results for the patient.

An objective measure for quantifying urine loss over a given time period includes the weighing of absorbent pads worn for certain time periods or during given daily activities, or outlining minor leakage on a paper towel. However, neither of these methods quantifies the instantaneous flow rate. In addition, they do not measure the number of leakage episodes occurring during daily activities, in a cognitively-impaired individual, and/or in a person who is unresponsive, for example.

Existing uroflowmeters are mostly laboratory- or clinic-based and involve asking the patient to sit on a commode as he or she would on a toilet. There are different methods to measure the micturition profile via this toilet- or urinal-based uroflowmetry. Prior art includes instrumented toilets developed to collect and analyze urine specimens with minimal intervention during micturition, and urinal style uroflowmeter stations. In some instances, a semi-portable uroflowmeter consisting of a unisex urinal mounted on caster wheels has been used. In some instances, a uroflowmeter in the form of a handheld pitcher-like container that measures the weight of the urine collected via a scale integrated into its base has been used. By deriving the weight change over a given time period, the voiding flow rate may be calculated. However, such devices can have inaccurate, noisy, variable outputs, for example, when the container moves and scale readings are affected by the accelerations associated with those movements. Additionally, the momentum of the urine stream on the scale may result in sharp fluctuations in the flow rate readouts. Another example uroflowmeter includes a sensor integrated in tubing attached to a collection funnel attached to the commode-style toilet or even the hospital bed. However, such devices are still toilet based and stationary, and do not lend themselves to measurements during daily activities, in a cognitively-impaired individual, and/or in a person who is unresponsive, for example. In addition, such devices use conductivity of the urine to measure the flow rate and, thus, if the salinity of the urine changes due to body dehydration or other symptoms, artifacts in flow rate may be introduced into the measurements.

Moreover, at least some of the aforementioned uroflowmetry devices cannot accurately assess urine leakage during walking, sleeping or rising from a chair because, in the aforementioned uroflowmetry devices, posture of the patient is limited only to the hips flexed at 90 degrees relative to an upright torso. In addition, because in women the labia can act as a reservoir to store urine between them, especially with small volumes of leakage, none of the prior art offers direct measures of the urine leakage flow rate or volume from the urethral meatus itself. Further, none of the aforementioned uroflowmetry devices presents an accurate and reliable solution for measuring the flow rate or volume of urine leakage episodes during daily activities, with a cognitively-impaired individual, and/or with a person who is unresponsive, for example, using wearable instrumentation.

SUMMARY

Disclosed are example uroflowmetry systems having wearable uroflowmeters, and methods of operating the same that measure and record urine leakage information for urine leakage episodes as they occur during daily activities, in cognitively-impaired individuals, and/or in persons who are unresponsive, for example. A disclosed example uroflowmetry system comprises a wearable uroflowmeter that attaches to a wet, mucous membrane inside the labial vestibule, and/or a smooth, non-mucous membrane of the penis. The wearable uroflowmeter includes: a funnel portion (e.g., having a funnel shape, a bowl shape, a hollow cone shape, etc.) having an end configured to secure the funnel portion against a person, an outlet opposite the end, and a funnel configured to capture urine excreted by the person when the end is secured against the person, and to direct the captured urine into the outlet; a fluid passage portion having an opening configured to receive the urine from the outlet of the funnel portion, and a fluid channel to pass the received urine along a length of the fluid passage portion; and a measuring portion having a sensor in the fluid channel configured to collect one or more measurements of the urine as the urine passes the sensor, the measurements representative of one or more properties and/or flow characteristics of the urine. Example flow characteristics include a urine flow rate, a volume of urine expressed during a micturition or urine leakage episodes. Example urine properties include temperature, salinity, pH, sign of infection, blood in urine, cells in the urine, cell derivatives in the urine, proteins in the urine, disease-specific biomarkers in the urine, hormones in the urine, etc., and/or a sensitivity, dynamic range, etc. thereof. The end fits over the urethral meatus and is attached directly or indirectly via adhesive, a vacuum, a condom, or by suspensory straps. Using instantaneous fluid velocities, a data logger can calculate instantaneous urine flow rates and/or velocities, as well as a maximum urine flow rate and/or velocity, and a volume of urine passing through the fluid channel past the sensor during a given time period. Use of a temperature sensor can be used to improve the accuracy of these measurements.

In some aspects of this disclosure, a wearable uroflowmeter is coupled to a wearable data logger that includes a housing; a first interface configured to receive a first conductor coupling the sensor to the data logger; a second interface configured to couple the data logger to a data analyzer, wherein the second interface is at least one of a port to receive a conductor, or a wireless transceiver; an analog circuit configured to process measurements taken by the sensor and received via the first interface to determine the one or more properties and/or flow characteristics of the urine; a non-volatile memory configured to store the one or more properties and/or flow characteristics of the urine; a first microcontroller to control the analog circuit and store the one or more properties and/or flow characteristics of the urine in the non-volatile memory; a display to present the one or more of the properties and/or flow characteristics of the urine; a button to control a functionality of the data logger; and at least one of a battery or a wireless power receiver to power the data logger.

In some aspects of this disclosure, a wearable data logger is coupled to a data analyzer that processes measurements collected by the data logger to provide diagnostic information to a user by comparing the one or more properties and/or flow characteristics of the urine with a pre-programmed pattern. The diagnostic information may be used to assist in determining a treatment for a patient's urinary incontinence. The data analyzer may process measurements taken by accelerometers, gyroscopic, magnetometer sensors, etc. to calculate a person's body orientation and body motion during urine leakage or voiding episodes to identify, reveal, correlate, etc. specific body motions, body orientations or daily activities associated with the urine leakage episodes.

A disclosed example method of operating a wearable uroflowmeter comprises: channeling urine excreted by a person through a funnel portion of a wearable uroflowmeter having an end to secure the funnel portion to the person; directing the urine channeled in the funnel portion through a fluid channel of the wearable uroflowmeter; and collecting a measurement of the urine with a sensor in the fluid channel of the wearable uroflowmeter, the measurement representing one or more properties and/or flow characteristics of the urine during a micturition or urine leakage event.

BRIEF DESCRIPTION OF THE DRAWINGS

FIG. 100 is a side cross-section view of the example wearable uroflowmeter of FIG. 10A.

Figure 1:
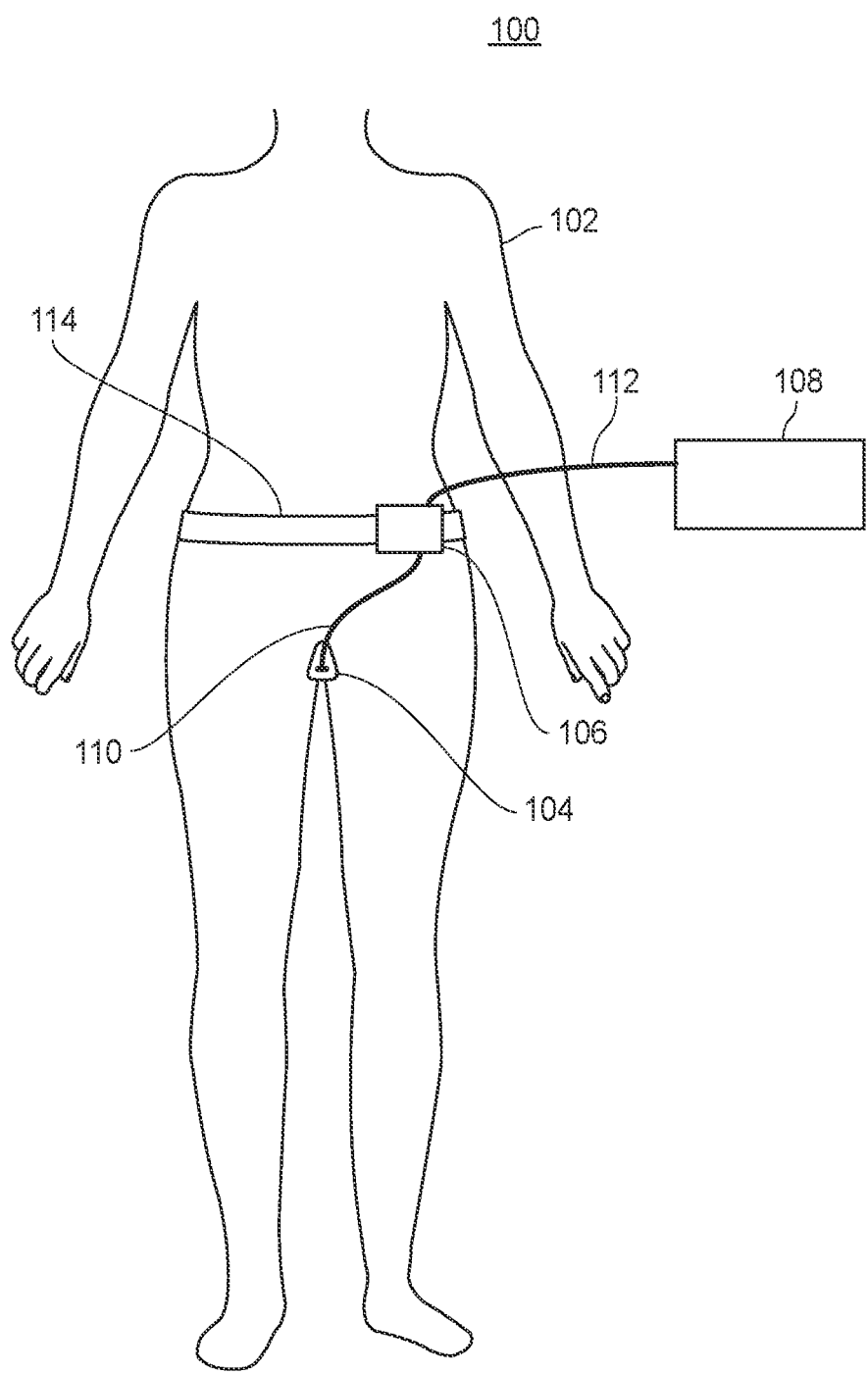
FIG. 1 illustrates an example uroflowmetry system including a wearable uroflowmeter constructed in accordance with this disclosure, and shown in an example environment of use.

The figures depict embodiments of this disclosure for purposes of illustration only. One skilled in the art will readily recognize from the following discussion that alternate embodiments of the structures and methods illustrated and disclosed herein may be employed without departing from the principles set forth herein.

In general, the same reference numbers will be used throughout the drawing(s) and accompanying written description to refer to the same or like parts. The figures are not to scale. Connecting lines or connectors shown in the various figures presented are intended to represent example functional relationships and/or physical or logical couplings between the various elements.

DETAILED DESCRIPTION

To reduce or eliminate some or all of the problems associated with conventional uroflowmetry, uroflowmetry systems having wearable uroflowmeters, and methods of operating the same, are disclosed. Disclosed uroflowmeters may be readily worn and can reliably measure urine flow properties and urine properties (e.g., intrinsic properties of the urine). Because disclosed uroflowmeters can be worn well beyond the length of a clinical visit, during daily activities, by cognitively-impaired persons, and/or by unresponsive persons, for example, they can be used to more fully, quickly and accurately diagnose and treat urinary incontinence. Accordingly, men and women suffering with urinary incontinence can have renewed hope that a treatment or management of their urinary incontinence can be identified. Moreover, because disclosed examples can be used to measure other urine properties such as resistance pH, sign of infection, blood in urine, hormones, etc., and/or a sensitivity, dynamic range, etc. thereof, disclosed examples can also be used to diagnose other urologic conditions, kidney diseases, etc. for which urine testing is instrumental.

When references are made herein to a sensor taking, collecting, etc. measurements it is to be understood that the sensor is forming one or more signals, currents, voltages, etc. that are representative of a property (e.g., temperature, flow rate, etc.) of a physical subject entity (e.g., urine). Such signals, currents, voltages, etc. formed by the sensor are further sensed, converted, processed, etc. (e.g., by an analog circuit of a data logging device, by an analog-to-digital converter, etc.) to derive the value of the actual property (e.g., temperature, flow rate, etc.). The terminology of a sensor taking, collecting, etc. measurements reflect that it is the sensor that is in physical communication with the physical subject entity.

While disclosed examples are described with reference to humans, aspects of this disclosure may be used by veterinarians to perform uroflowmetry for non-humans, for example, for other types of mammals.

Reference will now be made in detail to non-limiting examples, some of which are illustrated in the accompanying drawings.

FIG. 1 is a front view of an example uroflowmetry system 100 having certain components that can worn by a person 102. In other embodiments (not shown in FIG. 1), certain components of the uroflowmetry system 100 are instead worn anywhere on the waist of the person 102, such as on their torso, for example. The example uroflowmetry system 100 includes an example wearable uroflowmeter 104, an example wearable data logger 106, and an example data analyzer 108. In the illustrated example of FIG. 1, the wearable uroflowmeter 104 is electrically coupled to the data logger 106 via one or more conductors of a cable 110, such as a universal serial bus (USB) cable. In some examples, the cable 110 is fixedly and sealably attached to the wearable uroflowmeter 104 to prevent conductors of the cable 110 from coming in contact with urine, to maintain hygiene, signal integrity, safety, etc., increase comfort during wearing, decrease size, etc. Alternatively, the wearable uroflowmeter 104 can be coupled to the data logger 106 wirelessly using a transceiver and/or interface implementing, for example, a Bluetooth®, near-field communication (NFC), or other suitable wireless communication protocol.

In the illustrated example of FIG. 1, the data logger 106 is coupled to the data analyzer 108 via one or more conductors of a cable 112, such as a USB cable. Alternatively, the data logger 106 can be coupled to the data analyzer 108 using a wireless transceiver and/or interface implementing, for example, a Bluetooth, NFC, wireless fidelity (Wi-Fi®), cellular, or other suitable wireless communication protocol. In some examples, the data logger 106 communicates with the data analyzer 108 via another device, such as a smartphone of the person 102. In the illustrated example of FIG. 1, the data logger 106 is worn on a belt 114, but could be worn in a sling, in a harness, carried in a pocket or purse, etc. An example location of the data logger 106 is over a bony landmark such as the iliac crest or sacrum. With miniaturization, the data logger 106 may be integrated together with the wearable uroflowmeter 104 and may use, for example, a secure digital (SD) card or wireless technology (NFC, Bluetooth, Wi-Fi, etc.) to transfer collected measurements to the data analyzer 108. In some examples, the data logger 106 includes a temperature compensation circuit to compensate for fluctuations in temperature caused by presence and absence of clothing, weather conditions and activity level.

In some examples, the uroflowmeter 104 and/or the data logger 106 provide feedback to the person 102 when urine leakage occurs (and possibly indicating how much leakage occurs). Example feedback includes a sound, auditory feedback to ear buds, haptic feedback, etc. Such so-called "biofeedback" can be useful for behavioral modification or changing their incontinence product. For example, in patients with stress urinary incontinence such leakage episodes often occur when sneezing, coughing, laughing, rising from a chair or lifting, etc. The wearer can then use that leakage information feedback to change her/his behavior the next time, by remembering to contract her/his pelvic floor muscles (a.k.a., the "Knack" maneuver) just before that leakage-provoking activity and to hold that contraction through that activity to prevent leakage. Thus, she or he learns, through the use of biofeedback, to reduce the frequency and severity of leakage episodes. In an example clinical intervention run by a physician, nurse or physical therapist, baseline leakage data before teaching the Knack is collected, and then improvements in the leakage episode frequency/amount may be monitored every two weeks, say, for 12 hours at a time and over the next several months (e.g., using a system like a cardiac Holter monitor).

Figure 2:
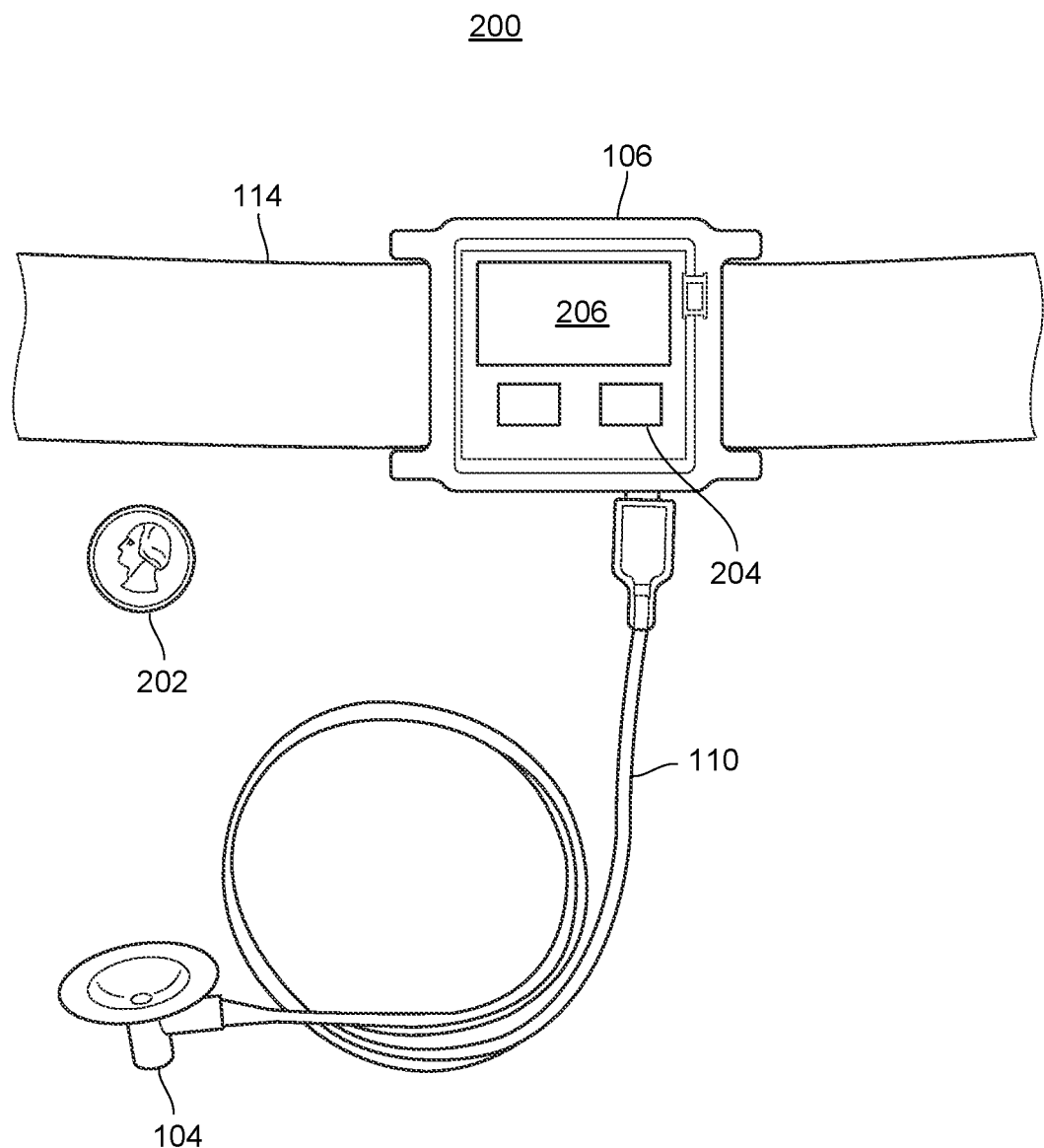
FIG. 2 is an image of an example implementation of components of the wearable uroflowmetry system of FIG. 1.

FIG. 2 is an image 200 of an example implementation of the wearable uroflowmeter 104, the cable 110, the data logger 106, and the belt 114. In the example of FIG. 2, the cable 110 is a USB cable that plugs into the data logger 106. In FIG. 2, a quarter 202, which is not part of a wearable uroflowmetry system, is shown for scale. In the illustrated example of FIG. 2, the data logger 106 includes one or more buttons, one of which is designated as reference number 204, and a display 206. The display 206 can be a liquid crystal display (LCD), a cathode ray tube (CRT) display, a light emitting diode (LED) display, an organic light emitting diode (OLED) display, an in-place switching (IPS) display, a touch screen, etc. The data logger 106 may include an event logger the patient could use to indicate symptoms, activities, etc?

Returning to FIG. 1, as will be discussed further below in connection with FIGS. 3A-3D, FIGS. 10A-10H, FIGS. 11A-11B, FIGS. 12A-12B, and FIGS. 13A-13B the wearable uroflowmeter 104 includes one or more sensors in a fluid channel to collect one or more measurements of urine as the urine passes the sensor(s). The measurements represent one or more properties of the urine, one or more flow characteristics of the urine, etc. Example flow characteristics include a urine flow rate, a urine flow velocity, a volume of urine expressed, etc. during a micturition or urine leakage episode. Example urine properties include temperature, salinity, pH, sign of infection, blood in urine, etc., and/or a sensitivity, dynamic range, etc. thereof. The wearable uroflowmeter 104 includes an end (e.g. that includes a flange, a rim, an edge, a lip, etc.) that conforms to a urethral meatus without gapping and is attached directly or indirectly via adhesive (e.g., a mucoadhesive, a mussel adhesive protein, a biomimetic material, etc.), tape, an absorbent dressing, a vacuum, a condom, by suspensory straps, etc. When the patient has body folds due to, for example, a higher body mass index (BMI), the body folds can be allowed to naturally conform to the wearable uroflowmeters described herein for comfort and increased stability during activities of daily living to provide a better seal of wearable uroflowmeter to the patient's body. Additionally and/or alternatively, the requirements for tape, adhesive, etc. may be reduced.

The wearable data logger 106 logs, collects, stores, etc. measurements collected, taken, etc. by the wearable uroflowmeter 104 in, for example, a tangible or non-transitory computer- or machine-readable memory or storage device (s). The data logger 106 periodically and/or aperiodically transfers logged measurements to the data analyzer 108 for analysis.

The data logger 106 may include one or more positional sensors to measure positional information for the person 102. Example positional sensors include a magnetometer sensor, an accelerometer sensor, a rate gyro sensor, a global positioning satellite (GPS) receiver, an altimeter sensor, an inertial measurement unit (IMU) to take inertial measurements including three-dimensional (3D) sensing of accelerations, 3D sensing of angular rates, and/or 3D sensing of the orientation, etc. Measurements taken by the positional sensors are stored together with the urine-related measurements. The data logger 106 may further include an additional IMU positioned on an abdomen to measure movements of the abdominal wall so that coughing, sneezing, crying, and laughing, activities known to be associated with stress urinary incontinence can be correlated with the leakage volume and rate. In some examples, the data logger 106 implements a standby mode to, for example, save battery life. The standby mode may be interrupted by a presence of urine forming a voltage across the filaments sensor(s) (described below in connection with FIG. 5) that activates the data logger 106.

The data analyzer 108 processes, analyzes, etc. the measurements collected by the data logger 106 to provide diagnostic information to a user (e.g., a medical professional) by, for example, comparing sensor measurements with pre-programmed patterns. For example, the data analyzer 108 can report a flow rate and/or velocity history containing instantaneous flow rates and/or velocities measured over time, and the largest instantaneous flow rate and/or velocity. The diagnostic information may be used, for example, by a user (e.g., a medical professional) to determine a treatment for a patient's urinary incontinence. For example, inadvertent urine loss can be measured via the velocity profile and volume lost during any leakage episode. Over a 24 hour period the number and severity of the leakage episodes can be measured. That information could be used by a physician to make recommendations for a course of treatment, whether behavioral, pharmacological, and/or surgical. The wearable uroflowmeter 104 can then be used to quantify the efficacy of the treatment.

The data analyzer 108 may additionally or alternatively process inertial measurements to calculate a person's body orientation and body motion during urine leakage or voiding episodes to identify specific body motions, body orientations or daily activities that led to urine leakage episodes. For example, flow characteristics can be used to identify that the person 102 often leaks when their foot hits the ground during walking, as identified from the time history of the waist worn accelerometer. Similarly, for running, the accelerations would be higher than walking and clearly identifiable as representing running rather than walking, shuffling or sitting. Coughing would have a characteristic acceleration profile at the waist and could similarly be recognized.

Any number and/or type(s) of techniques, methods, algorithms, etc. may be used to identify the physical activity of the person 102. For example, algorithms similar to those used for voice recognition on mobile devices. For example, a combination of one or more measurements by IMU, GPS, altimeter, etc. sensors recorded during different activities of daily living can be compared with known classified patterns (e.g., sitting, standing, walking, etc.) using machine learning, neural network, or deep learning techniques, for example. In a learning phase, known patterns can be learned by having subjects wear a data logger 106 on the same location on the waist and repetitively perform different activities. Signals are then collected from the data loggers 106, filtered, and post processed to obtain secondary key information unique to each type of activity. The post processing and time frequency analyses may include, for example, Fourier, wavelet transformations, histogram plots, and scalogram plots. After post processing and labeling signals, a neural network model may be used to learn signal patterns indicative of different activities. After this learning phase, the neural network model can be loaded on the waist worn data logger 106 and used to identify the type of new activities.

In some instances, a wearable uroflowmeter may become wholly or partially unattached from the patient. Such events may be detected by the data logger 106 and/or the data analyzer 108 by detecting a change in measurements (e.g., a drop in measured volume, etc.). In some instances, a sufficient amount of urine is captured to correlate leakage events with different activities, even if the total amount of urine is inaccurate. Thus, in some examples, it may be acceptable to have a partial seal of the wearable uroflowmeter at the patient.

Figure 8:
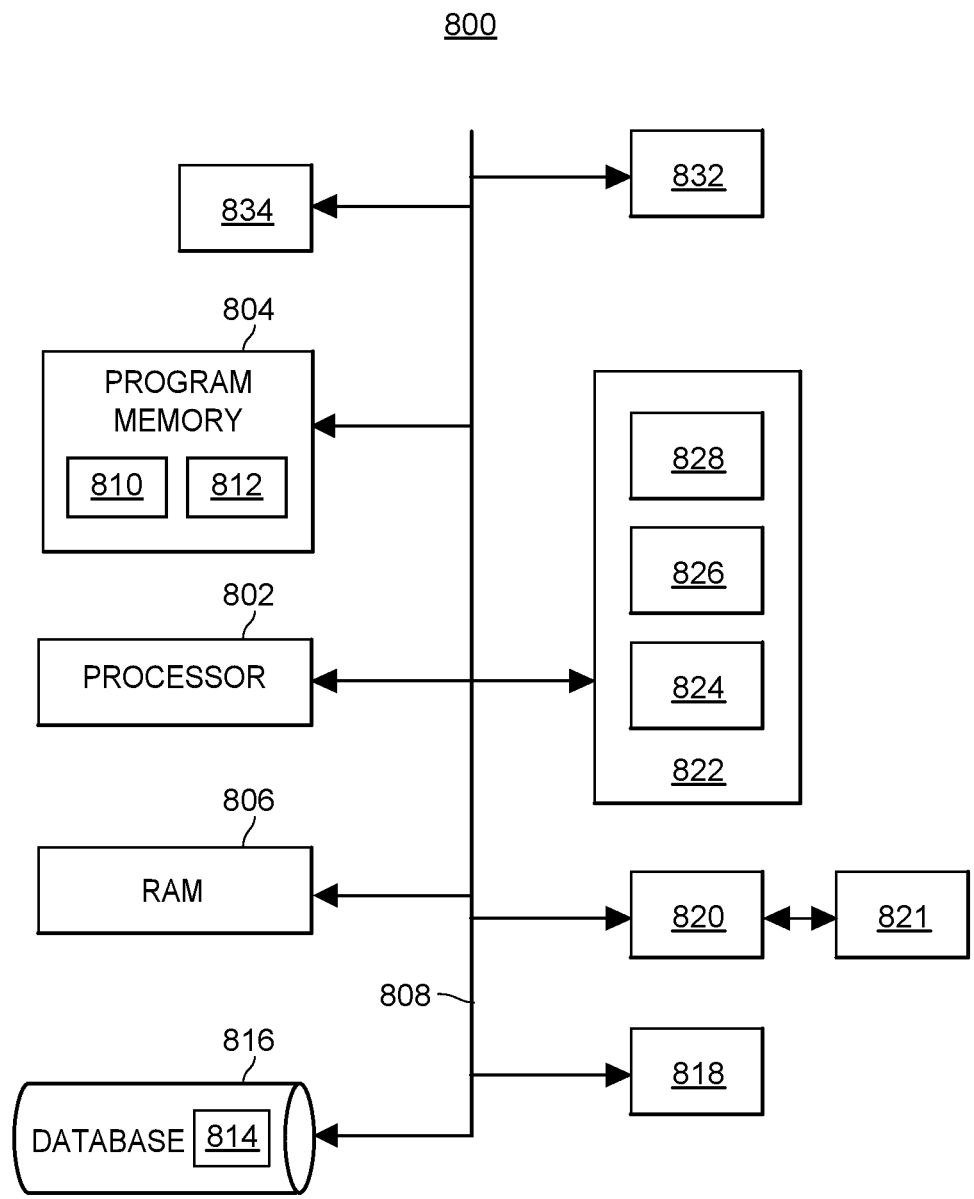
FIG. 8 is a block diagram of an example computing system that may be used to implement the example data logger of FIG. 1.

In some examples, the data analyzer 108 is a personal computer, a laptop, a tablet, a workstation, etc. having, among other things, a processor and a tangible non-transitory computer- or machine-readable storage disk or other memory storing machine- or computer-readable instructions that, when executed by the processor, cause the data analyzer 108 to carry out any of the methods, steps, operations, etc. disclosed herein. An example computing system 800 that may be used to implement the data analyzer 108 is shown in FIG. 8.

While a uroflowmetry system 100 is shown in FIG. 1 and FIG. 2, one or more of the elements, components, devices, etc. illustrated in FIGS. 1 and 2 may be combined, divided, re-arranged, omitted, eliminated or implemented in another way. For example, some or all of the analysis performed by the data analyzer 108 may instead be performed by the data logger 106. As another example, the wearable uroflowmeter 104 may be integrated with the data logger 106. As another example, the uroflowmetry system 100 may include one or more elements, components, devices, etc. in addition to, or instead of, those illustrated in FIGS. 1 and 2, or may include more than one of any or all of the illustrated elements, components, devices, etc.

Figure 3A:
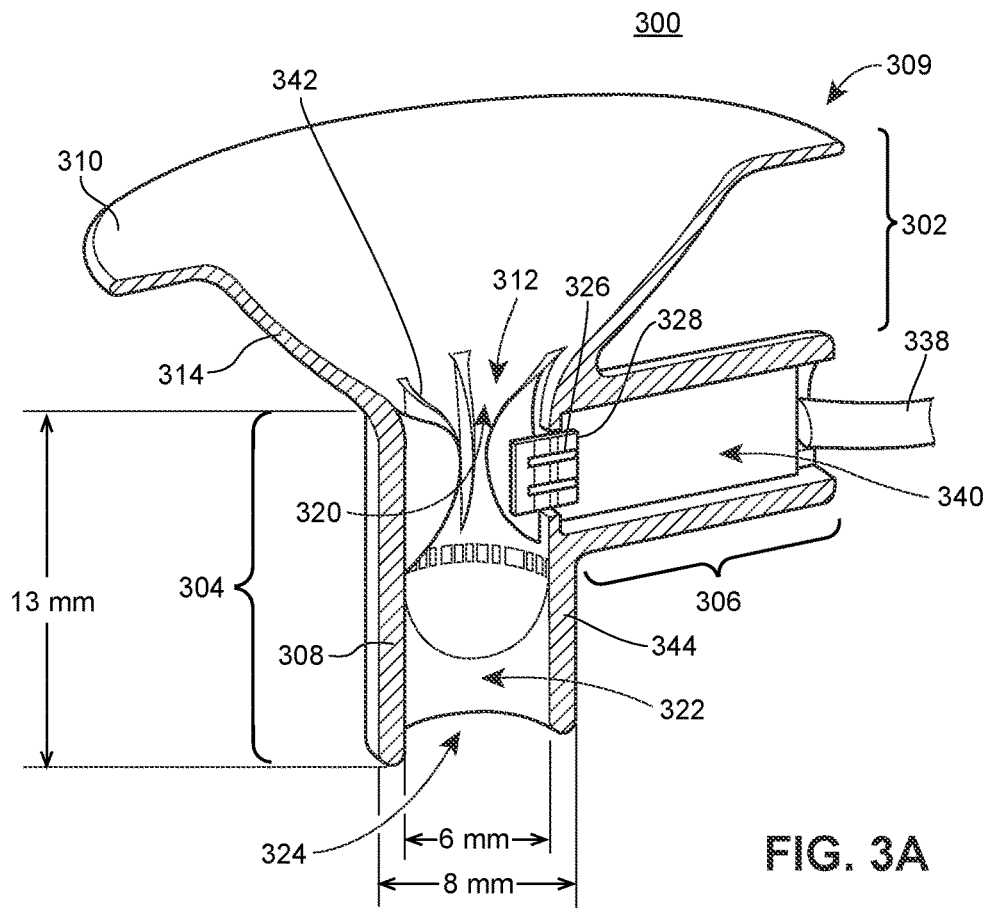
FIG. 3A is an off-axis cross-section view of an example wearable uroflowmeter for a female that may be used in the example uroflowmetry system of FIGS. 1 and 2.
Figure 3B:
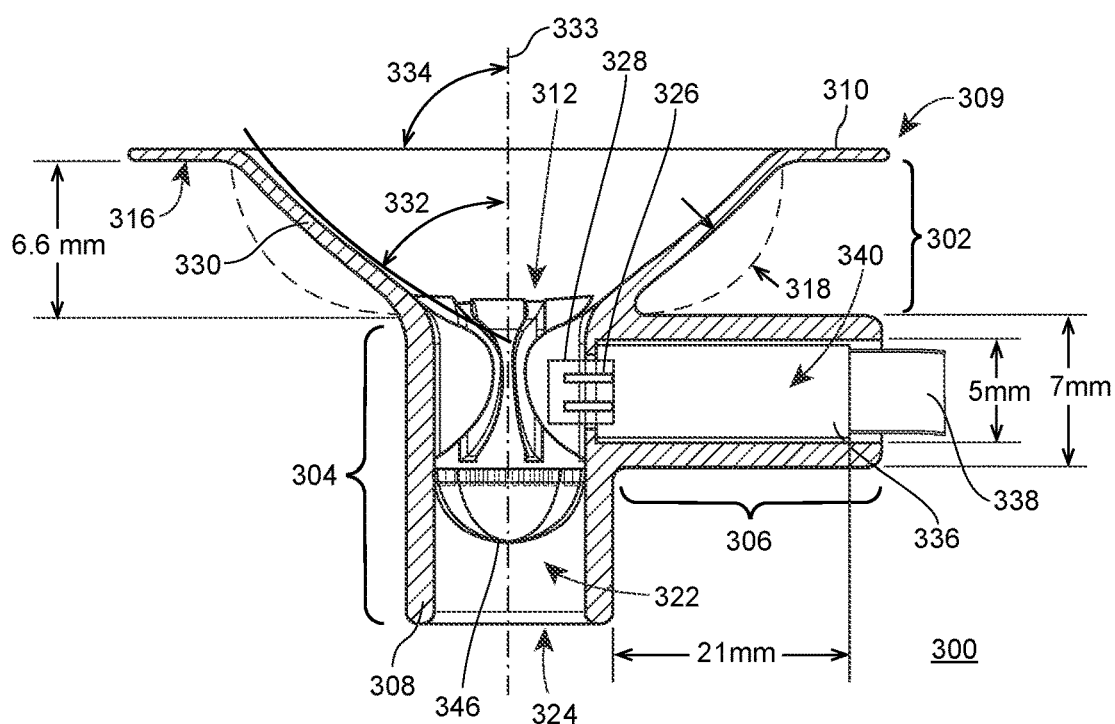
FIG. 3B is a side cross-section view of the example wearable uroflowmeter of FIG. 3A.
Figure 3C:
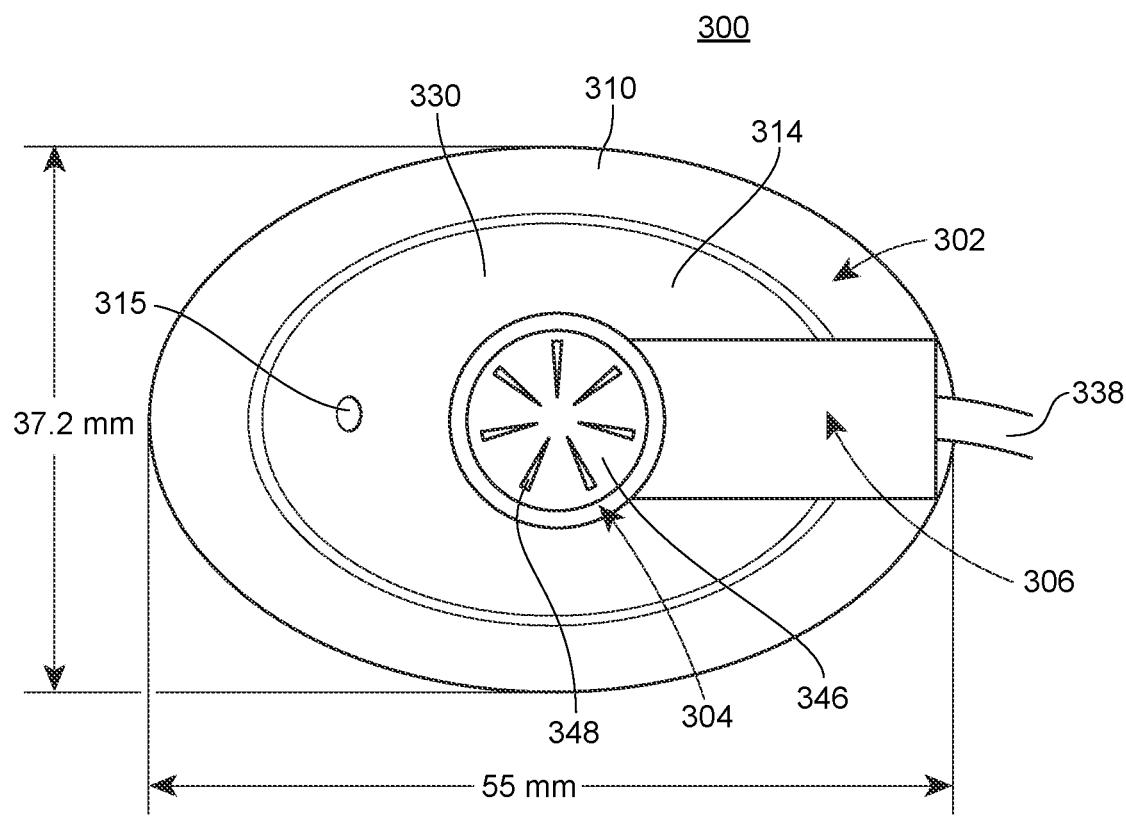
FIG. 3C is a bottom view of the example wearable uroflowmeter of FIG. 3A.
Figure 3D:
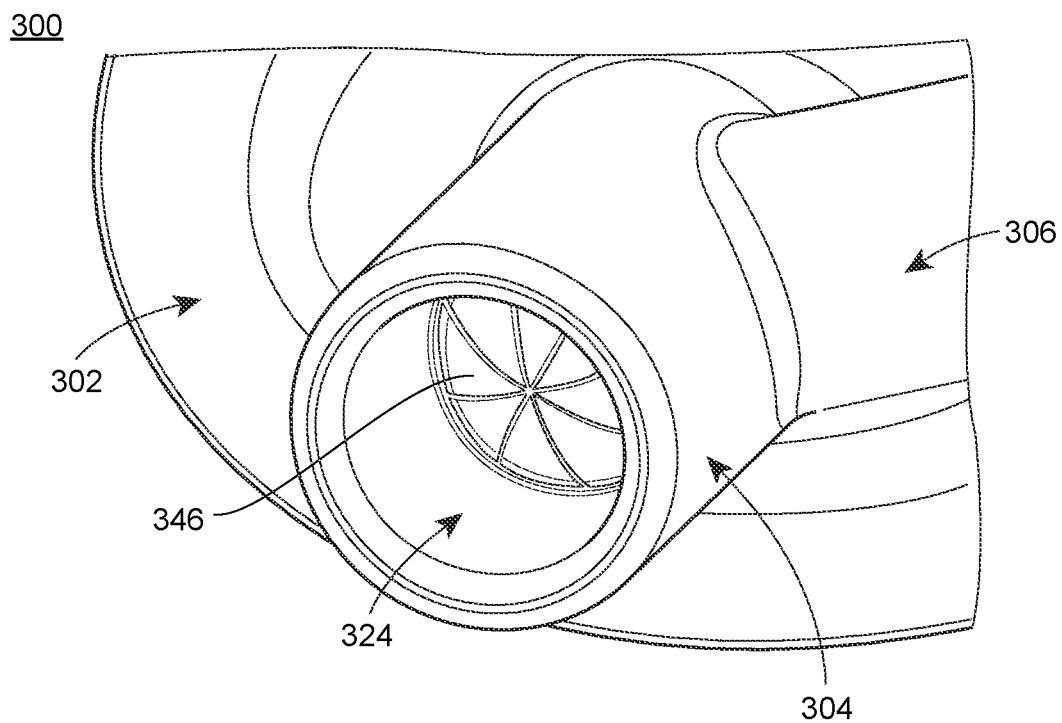
FIG. 3D is a bottom off-axis view of the example wearable uroflowmeter of FIG. 3A.

FIG. 3A is an off-axis cross-section view of an example wearable uroflowmeter 300 for a female that may be used to implement the example wearable uroflowmeter 104 of FIGS. 1 and 2. FIG. 3B is a side cross-section view of the example wearable uroflowmeter 300. FIG. 3C is a bottom view of the example wearable uroflowmeter 300. FIG. 3D is a bottom off-axis view of the example wearable uroflowmeter 300. For clarity of illustration, a reference number may not be shown in all of the FIGS. 3A-3D.

The example wearable uroflowmeter 300 includes a funnel portion 302, a fluid passage portion 304 and a measuring portion 306. As shown in FIGS. 3A-3D, the funnel portion 302, the fluid passage portion 304 and the measuring portion 306 may be portions of a unitary housing 308.

The funnel portion 302 has an end 309 that may include, for example, a flange 310, a lip, a rim, an edge, etc., to secure the funnel portion 302 to a person, an outlet 312 opposite the end 309, and an intervening funnel 314 to capture urine excreted by a person into the outlet 312. In an example, the flange 310 has an oval shape that is 55 millimeters (mm) long (see FIG. 3C)×37.2 mm wide (see FIG. 3C), and the funnel 314 is 6.6 mm tall (see FIG. 3B). Of course other dimensions may be used. For example, a length of 10 to 30 mm, a width of 5 to 15 mm, and a height of 2 to 15 mm. Such dimensions provide sufficient volume to accommodate urine flow rate associated with bladder emptying as well as leakage episodes. The flange 310 may be sized to ensure adequate fit and adhesion without causing discomfort. In some examples, the flange 310 is angled slightly downward to more comfortably fit and adhere to the labia. However, the funnel portion 302 and/or, more generally, the wearable uroflowmeter 300 may be formed according to different dimensions to, for example, accommodate patients of different sizes.

Figure 4:
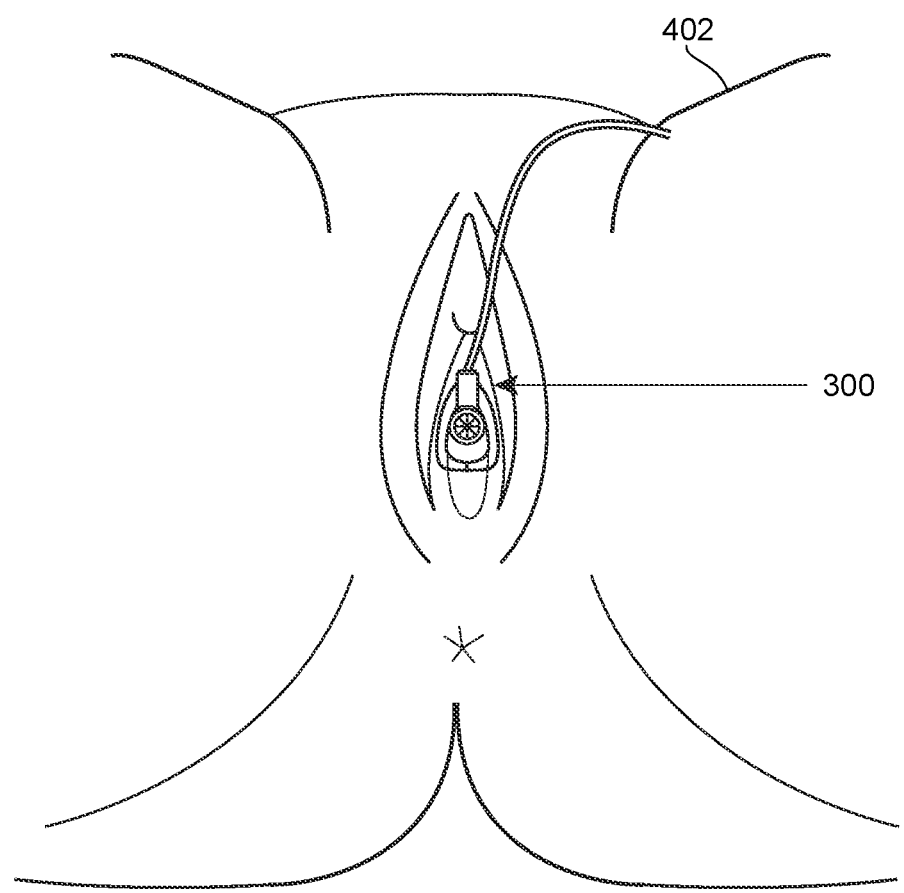
FIG. 4 illustrates an example positioning of the wearable uroflowmeter of FIGS. 3A-3D for a female in the lithotomy position.

While the wearable uroflowmeter 300 is worn, the funnel 314 is generally collinear with and proximate to the external meatus when the flange 310 is secured against a person. An example placement of the wearable uroflowmeter 300 over the external meatus of a female 402 is shown in FIG. 4. To improve wearability and accommodate different body shapes, the flange 310 may be formed to conform to or fit the shape of an external meatus without gapping or collapsing during sitting activities, a vestibule or a labia, with little gapping. Example pliable or flexible materials include a flexible polymer, a Formlabs® flexible resin, a Formlabs elastic resin, Nusil™ MED2-4220, Nusil MED4-4220, Nusil MED-4917, a Formlabs durable resin, etc. that can be formed to have different thicknesses and/or cured differently for different portions of the wearable uroflowmeter 300 to provide variable thickness and/or variable flexibility. In general, it is preferable that the device conforms to or fits the body and fits comfortable around the meatus, which aids in attachment and device stability. An example flange 310 is shaped to surround the urethra while not inhibiting sphincter change in shape during urination. An example flange 310 is bow shaped like the front of a boat to reduce cutting into the clitoris, which can be uncomfortable. If the bow shape is proximate the clitoris it may ride down the clitoris. In some examples, the flange 310 is a sturdy strip (e.g., of rubber, fabric, adhesive strip, etc.) that is attached to, laminated into, etc. the funnel 314 and accommodates moist surfaces. The flange 310 may be secured to a person using, for example, an adhesive (e.g., a mucoadhesive, a mussel adhesive protein, a biomimetic material, etc.), absorbent dressing (e.g., Nusil pressure sensitive adhesive, 3M™ 9943 Hydrocolloid Adhesive Medical Tape which preferably absorbs excess moisture, Polyurethane Backing, 80 #Liner, 3M Nexcare™ Tegaderm™ Transparent Film Dressing, etc.), tape, a dry adhesive (e.g., formed of micro-tipped suction cup pillars on a flexible substrate, gecko-inspired tape), or a vacuum formed between the flange 310 and at least one of external meatus, or an adjacent labia to form a preferably liquid-tight fit. When a vacuum is used, the funnel portion 302 may include a valve 315 (shown in FIG. 3C) to assist venting of the vacuum and release the flange 310. An adhesive dressing (not shown) may be applied around a non-adhesive surface 316 of the flange 310 and the surrounding skin. An example adhesive dressing is a hydrocolloid dressing. An undergarment, an absorbent pad, a suspensory strap, or other suitable securing means may be used to hold the flange 310 in place. To avoid injury or irritation to the external meatus, adhesive is preferably not applied to an interior of the funnel portion 302. The flange 310 is sized to support sufficient adhesion, while being small enough for comfort.

While the funnel portion 302 and flange 310 of FIGS. 3A-3D are shaped to fit against a female, the funnel portion 302 can instead have a shape similar to a sleeve, a condom, etc. if used by a male. In such examples, the funnel portion 302 can be flexible to conform to the shape of a penis. For example, see the example uroflowmeters for a male of FIGS. 11A-11B, 12A-12B and 13A-13B.

The funnel 314 may be formed of a rigid or stiff material. Alternatively, the funnel 314 is formed of a flexible or pliable material for comfort, to accommodate or be responsive to sudden pressure changes in the funnel 314 at, for example, the start of micturition, etc. This can reduce detachment of the flange 310 from the body due to a pressure spike associated with a sudden high urinary flow rate. A sensor (e.g., a strain gauge) measuring a change in a shape or deformation 318 of the flexible funnel 314 can be used together with a known pressure-volume relationship of the funnel 314 to calculate adjustments of the maximum peak flow rate measured in the presence of the flexible funnel 314. For example, as a shape of the funnel 314 changes responsive to pressure changes in the funnel 314, the volume of the funnel 314 changes (e.g., increases with increase pressure). In response, the flow rate out of the funnel 314 into a fluid channel 322 changes. Accordingly, the instantaneous flow rate and/or velocity measured by the sensor(s) 326 needs to be adjusted according to the known pressure-volume relationship of the funnel 314. The flange 310 may be formed of a material that is more flexible or pliable than another material used to form the funnel 314. However, when the funnel 314 is flexible to accommodate pressure changes, the funnel 314 may be more flexible than the flange 310. An example funnel 314 has a shape that comfortably fits within the range of the labial vestibule (e.g., elongated with narrower width). The example funnel 314 can be compressible or deformable for comfort, but not overly compressible to the point where it could easily collapse. Wearable uroflowmeters may come in different sizes and/or shape depending on the size of the wearer.

The fluid passage portion 304 includes an opening 320 to receive urine from the funnel portion 302 through the outlet 312, and a fluid channel 322 to pass the urine along the length of the fluid passage portion 304 and exit through an outlet 324 of the fluid passage portion 304 and/or, more generally, the example wearable uroflowmeter 300. In some examples, tubing is attached to the outlet 324 to drain urine into a pad or drainage bag (not shown).

The measuring portion 306 includes one or more sensors (one of which is designated at reference numeral 326 in FIG. 3B) that extend into the fluid channel 322 to collect one or more measurements of the urine as the urine passes the sensor(s) 326, the measurements are representative of a property of the urine, and/or a flow characteristic of the urine. In general, having the sensor(s) 326 in the middle of the fluid channel 322 at close to the outlet 324 places the sensor(s) 326 in the highest velocity region of the flow and, thus, produces the highest dynamic range if the entire channel is filled with fluid. Closer to the wall 344 of the fluid channel 322 increases the probability that a low flow rate stream that forms adheres to the wall may be detected but the flow rate approaches zero. Therefore, the distance can be chosen based on the flow rate and the desired dynamic range. In some examples, the sensor(s) 326 extend 2 mm into the fluid channel 322. Of course, other dimensions may be used. As discussed in more detail in connection with FIG. 5, the sensor(s) 326 are implemented on a substrate 328 (e.g., a non-conductive substrate such as a glass substrate) that extends into the fluid channel 322. As will be described further below, the fluid channel 322 has a known cross-section area at or in the vicinity of the substrate 328. In an example shown in FIG. 3A, The example fluid channel 322 of the illustrated example of FIG. 3A has a cylindrical shape that is 8 mm outer diameter x 6 mm inner diameter x 13 mm tall. Of course, other dimensions may be used. For example, the fluid channel 322 may have an inner diameter of 6-12 mm and a wall thickness of 0.5-2 mm. However, the fluid channel 322 and/or, more generally, the wearable uroflowmeter 300 may be formed according to different dimensions to, for example, accommodate patients of different sizes.

To improve accuracy, the fluid channel 322 in the vicinity of the substrate 328 is preferably rigid so the cross-section area in the vicinity of the substrate 328 is constant. However, it may be flexible as long as the cross-section area in the vicinity of the substrate 328 is generally constant (e.g., a change from a circle to an ellipse). In some examples, flow rate can be accurately measured for flow rates between 1 milliliters (ml)/second to 35 ml/second. The fluid channel 322 and the funnel portion 302 are preferable kept as short as feasible to increase comfortability and to reduce the possibility that clothing, etc. causes the wearable uroflowmeter 300 from becoming detached or interferes with the wearable uroflowmeter 300. The length of the fluid channel 322 can be kept shorter than the labia for comfort.

As best seen in FIG. 3B, a wall 330 of the funnel 314 is disposed at a first angle 332 relative to a longitudinal axis 333 (e.g., at an acute angle) of the fluid channel 322 to direct urine into the fluid channel 322, and the flange 310 is disposed at a second different angle 334 and projects outward from the longitudinal axis 333 (e.g., perpendicularly).

The measuring portion 306 includes a sensor assembly 336 that includes the substrate 328, the sensor(s) 326, and a flexible cable 338 having one or more conductors. The sensor assembly 336 is disposed in a compartment 340 of the measuring portion 306. The sensor assembly 336 is sealed into the compartment 340 to, for example, prevent conductors of the cable 338 from coming in contact with urine, to maintain hygiene, signal integrity, safety, etc. The compartment 340 securely holds the sensor assembly 336 in the compartment 340 and, thus, holds the sensors(s) 326 securely in the fluid channel 322. The compartment 340 also routes the cable 338 to the sensor assembly 336. However, the sensor assembly 336 and the sensor(s) 326 may be held with some flex to accommodate movements of a person wearing the wearable uroflowmeter 300. In some examples, the sensor assembly 336 is angled by a small amount, relative to the longitudinal axis 333 of the fluid channel to reduce the formation of eddy currents over the sensors 326 and/or reduce flow separation. For example, the sensor assembly 336 may be angled by 9 degrees. The angle amount is small to avoid resistance to urine flow. As shown in FIG. 4, the cable 338 can be routed forward from the wearable uroflowmeter 300 to the data logger 106 worn on a belt, a strap, carried in a pocket, carried in a bag, etc. However, it may be routed rearward. In an example shown in FIG. 3B, the compartment 340 has a cylindrical shape that is 7 mm outer diameter×5 mm inner diameter×21 mm long. Of course, other dimensions may be used. For example, the compartment 340 may have length of 3 to 14 mm. In some examples, one or more of the sensor(s) 326 are disposed on a surface of the fluid channel 322. In some examples, the substrate 328 is held vertically on an edge where one sensor (e.g., a temperature sensor) is upstream from another sensor (e.g., a flow velocity sensor). To increase comfort, the compartment 340 may be formed of a pliable or flexible material for comfort and the compartment 340 angled. Alternatively, the sensor(s) 326 may be embedded in the wall of the fluid channel 322 and the measuring portion 306 eliminated. However, the compartment 340 and/or, more generally, the wearable uroflowmeter 300 may be formed according to different dimensions to, for example, accommodate patients of different sizes.

In some examples, to form a more laminar urine flow at the sensor(s) 326 and to reduce sensor performance, accuracy, etc. degradations due to turbulent urine flow, the fluid channel 322 includes one or more shaped structures (one of which is designated at reference numeral 342) in the fluid channel 322. An example shaped structure 342 is a vane, fin, mesh, hair-like structure, etc. oriented longitudinally in the fluid channel 322 positioned from the opening 320 past the substrate 328. An example vane 342 is substantially flat/planar with contoured edges, attaches to or is integral with a wall 344 of the fluid channel 322, and extends from the wall 344 into the fluid channel 322. As seen in FIG. 3A, multiple shaped structures 342 may be configured in a radial pattern around the longitudinal axis 333 (e.g., with even spacing), in a manner that causes the flow of urine to initially impinge upon the thin sides/edges of shaped structures 342 before traveling over/past the planar surfaces. In some examples, to avoid discomfort, the structures 342 are formed to not extend outside the fluid channel 322. In some examples, to reduce spiraling of urine within the funnel portion 314, the shaped structures 342 extend into the funnel portion 314.

When small amounts of urine are excreted, there may not be enough urine flowing past or present at the sensor(s) 326 to be accurately measured. In some examples, to help collect enough urine to encapsulate the sensor(s) (thereby enabling the sensor(s) 326 to sense urine properties), the fluid channel 322 includes a flow restrictor such as a membrane 346 in a vicinity of the outlet 324 of fluid channel 322. The membrane 346 helps maintain a linear correlation between urine velocity and urine flow velocity passing the sensor(s) 326, from zero to maximum flow. An example membrane 346 is a flexible membrane having a convex shape and slits 348 defined therein. In some examples, the membrane 346 is disposed fully or partially inside the fluid channel 322 to protect from deformations caused by surrounding tissues, clothing, etc. Alternatively, the membrane 346 is located fully outside the fluid channel 322 to reduce the resistance to urine flow and increase the capacity of the fluid channel 322. As the flow rate of urine increases, the slits 348 in the membrane 346 open, thereby allowing urine to pass. In some examples, the membrane 346 retains about 1 milliliter of urine under no flow conditions. One (1) ml represents a volume in the fluid channel 322 above the membrane 346 to at least the level of the sensor(s) 326. In some examples, the thickness of the membrane 346 (e.g., approximately 0.5 mm), material, dome shape, number of slits, and its star formation were determined empirically. However, they may be determined theoretically. The membrane 346 is selected to be flexible enough to reduce the pressure resistance during micturition, and at the same time elastic enough such that under flow rates of ~1 ml/s (minimum required value chosen as a design variable) would keep the fluid level inside the urine channel above the substrate 328 and sensor(s) 326.

The uroflowmeter 300 may be formed of biocompatible materials (e.g., a biocompatible Nusil MED2-4220 silicone elastomer). Instead of a membrane, other materials such as a micro net, a mesh or hair like structure may be used to form the flow restrictor. A hydrophobic coating, a wicking element or a tiny opening at the center to prevent or reduce urine retention, etc. may be used. In some examples, the uroflowmeter 300 is cleanable and/or sanitizeable. The uroflowmeter 300 may be intended for single use, or multiple use. In some examples, the uroflowmeter 300 is formed as a unitary body of a clear or opaque material.

In some examples, to accommodate a sudden high urine flow rate in some incontinent women with a full bladder, which might result in bypass leakage, the wearable uroflowmeters disclosed herein may include a bypass and/or a bypass valve such that only a portion of the urine flow passes the sensor(s) 326, in other words, increases urine flow out of the funnel portion under high urine flow conditions. Measured urine flow properties can then be appropriately scaled to determine (e.g., estimate, etc.) the total urine flow output by the patient.

Figure 7:
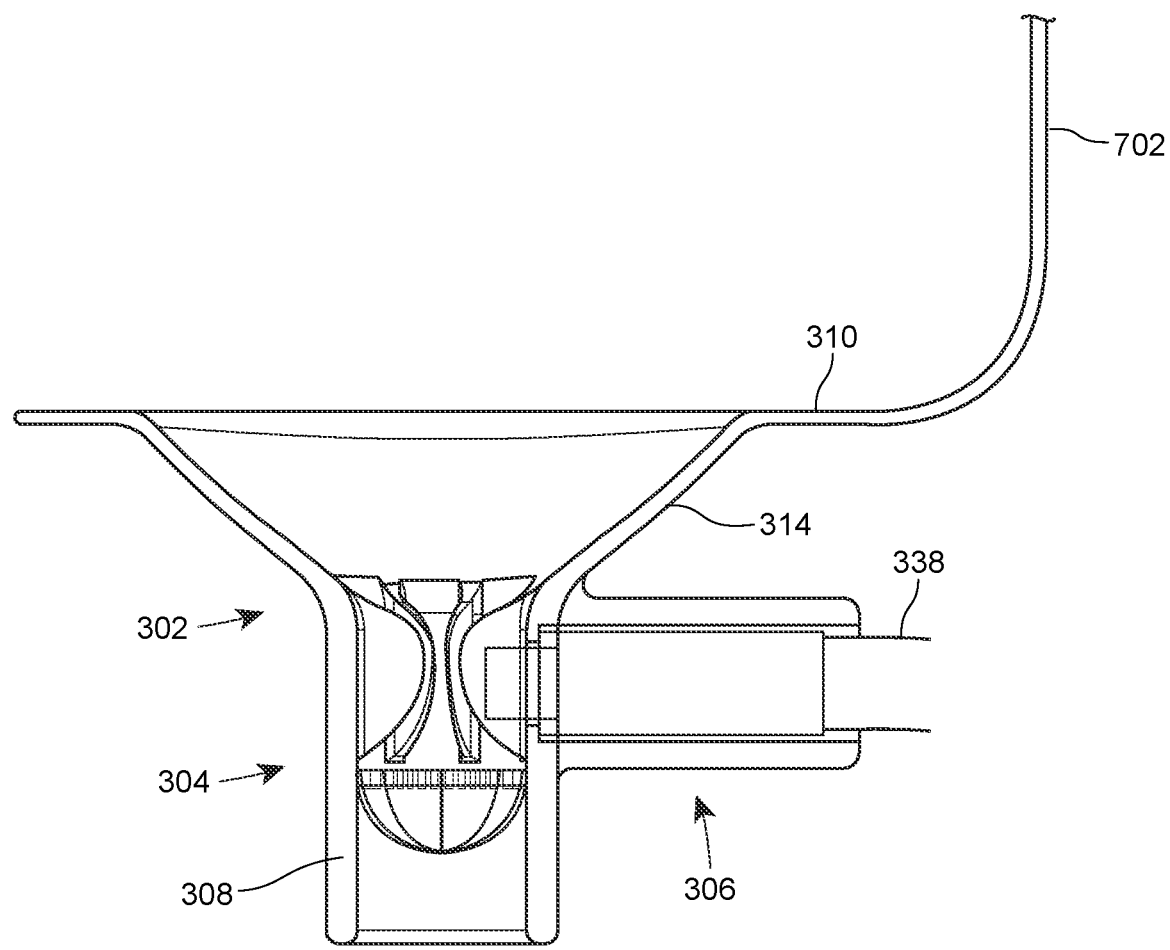
FIG. 7 illustrates an example modification of the wearable uroflowmeter of FIG. 3A-3D that includes an extension that is inserted in the vaginal vestibule as the wearable uroflowmeter is positioned.

While a wearable uroflowmeter 300 is shown in FIGS. 3A-3D, one or more of the elements, components, devices, etc. illustrated in FIGS. 3A-3D may be combined, divided, re-arranged, omitted, eliminated or implemented in any other way. For example, the fluid channel 322 may be shortened such that the fluid channel 322 is formed by or at the outlet 312 of the funnel portion 302. Further, the wearable uroflowmeter 300 may include one or more elements, components, devices, etc. in addition to, or instead of, those illustrated in FIGS. 3A-3D, or may include more than one of any or all of the illustrated elements, components, devices, etc. For example, as shown in FIG. 7, the flange 310 may include an extension 702 that can be inserted in the distal vaginal vestibule (preferably not past the hymen) as the wearable uroflowmeter 300 is positioned to provide additional stability to the wearable uroflowmeter 300 as it is worn. The extension 702 to be held in place by an adhesive, a vacuum, an undergarment, an absorbent pad, a suspensory strap, or other suitable means for securing the wearable uroflowmeter 300 to a person. Further, the flange 310 can have other shapes such as a circular shape, a triangular shape, a teardrop-like shape where the larger end is shaped to better fit female anatomy, to accommodate anatomy differences due to prolapse or folds (e.g., due to a higher BMI), etc. Further still, wearable uroflowmeters with deeper funnels may be used to accommodate, for example, a patient with urethral prolapse. Moreover, the funnel 314 and the fluid channel 322 can be formed by a thru hole in a flexible polymer sheet. In an example, the sensor assembly 336 can be formed within the polymer sheet, with its sensor(s) extending into the through hole. In another example, the sensor assembly 336 is in a housing attached to the bottom of a polymer sheet and the housing includes a fluid channel beneath the thru hole. The polymer sheet may include a shallow funnel attached to its top surface.

Figure 5:
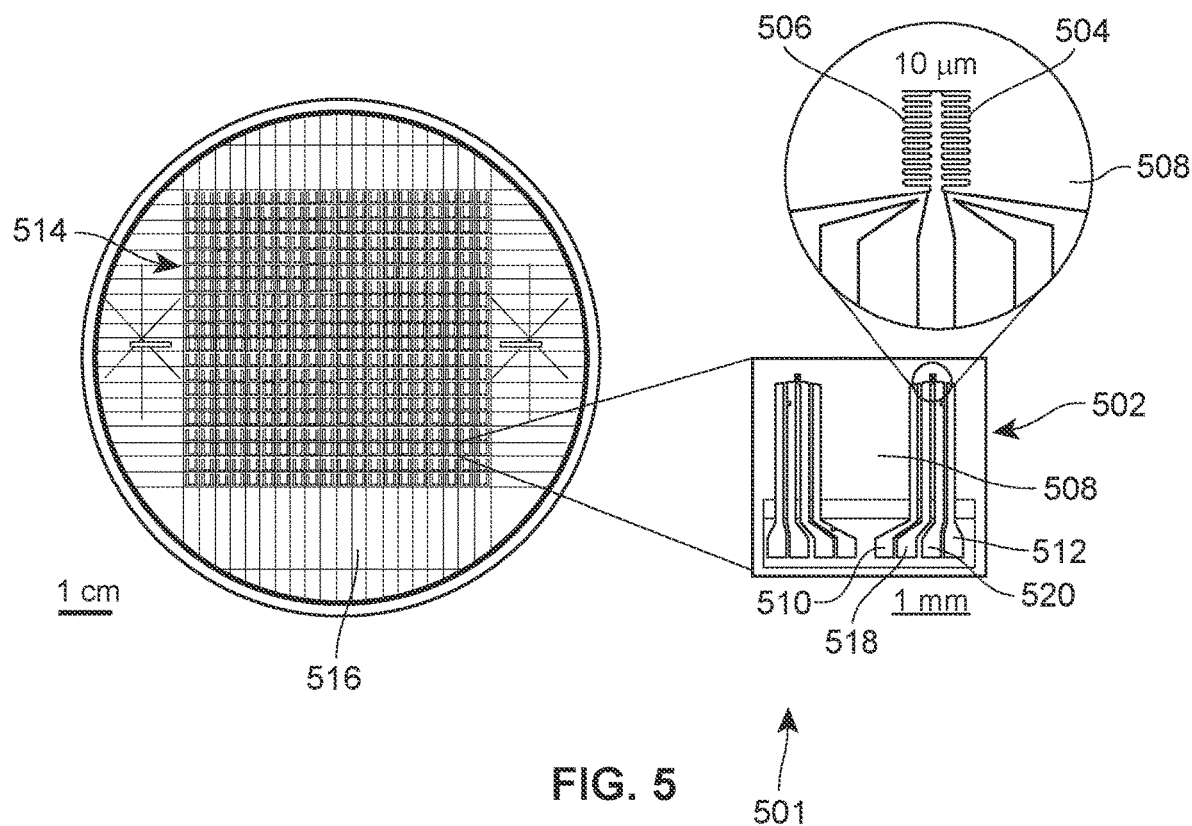
FIG. 5 illustrates example sensors for the example wearable uroflowmeters disclosed herein.

Turning to FIG. 5, example sensors 501 and 502 that may be used to implement the sensors disclosed herein (e.g., the example sensor(s) 326) are shown. The example sensor 502 is a planar 3 mm (length)×3 mm (width)×1 mm (thick) micro-electro-mechanical system (MEMS) sensor. The sensor 502 includes two planar filaments 504 and 506 that lie on a surface of substrate. The filaments 504, 506 are each formed of layers of Pt/Ti (platinum/titanium) deposited on a 0.6 mm thick glass substrate 508. Other applicable alloys and/or dimensions may be used. While the filaments 504, 506 are formed according to a planar rectangular zig-zag pattern, other patterns may be used. While the filaments 504, 506 are intended to be identical, they may differ due to, for example, manufacturing tolerances. The filament 504 measures temperature, and the filament 506 measures urine flow velocity, or vice versa. The filaments 504, 506 of the sensor 502 can operate independently, and their outputs combined to provide a more accurate measurement after post processing. The Pt/Ti filaments 504, 506 are covered by a protective layer to electrically isolate the filaments 504, 506 from the urine flow and surrounding walls. Example protective layers are glass and nitride films using a plasma-enhanced chemical vapor deposition (PECVD) technique.

The sensor 502 can operate as a hotwire sensor. The example sensor 502 uses constant current or constant temperature anemometry using a steady direct current (DC) current to measure the flow velocity or temperature of urine passing over the sensor 502. However, an alternating current and impedance measurement technique could be used. In operation, a constant or steady DC current is passed through each filament 504, 506, causing its respective temperature and respective resistance to increase. As a result, if the DC current is held constant, a voltage difference between terminals 510 and 512 of the sensor 502 is created. As urine passes over the sensor 502, the heat generated by the constant DC current is dissipated by the urine due to convection and the voltage difference changes. By measuring, amplifying and calibrating the voltage difference between the filaments 504, 506 for different combinations of known flow velocity and known temperature, fluid velocity can be determined. Knowing the cross-section area of the fluid channel 322 and urine flow rate, instantaneous fluid volumes passing through the fluid channel 322 can be calculated as the cross-section multiplied with flow velocity. Instantaneous fluid volumes can be combined to determine total flow volumes.

In some examples, a first dedicated DC current source between a terminal 510 to a terminal 512 drives the filaments 504, 506 of the sensor 502 with a 9 milliamp (mA) DC current to measure flow velocity, and a second dedicated DC current source between similar terminals drives the filaments (e.g., like filaments 504, 506, but too small to be seen in the illustration of FIG. 5) of the sensor 501 with a 0.5 mA DC current to measure temperature. The voltage difference across terminals 518 and 520 of the sensor 502 is sensitive to both fluid velocity (convection) and temperature of the fluid passing over the sensor 502. The voltage difference across similar terminals of the sensor 501 is principally sensitive to the temperature of the fluid because of its lower electrical current levels and, therefore, lower power input. An example overall resistance of the filaments 504, 506 taken together is approximately 570 ohms ((2), and the maximum voltage variations across the sensor 501, 502 may approximately 3 millivolts (mV). Example resistances of the terminals 510, 512, 518 and 520 is 50 Q. Alternatively, the sensors 501, 502 may be multiplexed to take two different measurements. For example, the sensors 501, 502 can be first excited with a 0.5 mA DC current to measure temperature during a first period of time, and then excited with a 9 mA DC current to measure temperature during a second period of time. In another example, a DC current source is positioned between the terminals 512 and 510 and between terminals 520 and 518, and the voltage difference between terminals 520 and 510 is measured, assuming terminal 520 is connected to ground.

As shown, the terminals 514 can be formed concurrently on a larger glass substrate 516. The glass substrate 516 can be cut to form smaller substrates (e.g., the substrate 508) having one or more of the sensors (e.g., the sensors 501 and 502).

To identify flow rates from a sensor output voltage, an empirical calibration process may be used. A selectively controllable pump pumps a fluid through a tubing into a wearable uroflowmeter constructed in accordance with this disclosure. The output of the uroflowmeter passes into a beaker that is placed on a scale. Readings taken by the scale over time are used to determine the output flow rate of the pump. Simultaneously, output voltages of a flow velocity sensor are collected. The flow velocity and output voltage data points can be combined to create a calibration curve for the sensor under test that represents flow velocity versus measured voltage. In some examples, points of the calibration curves are interpolated and/or extrapolated. In use, a measured voltage is used to determine a flow velocity using the calibration curve. The calibration curve may then be used by the data logger 106 and/or the data analyzer 108 to estimate, compute, etc. flow rates based on measured velocities. Note that the flow velocity multiplied with the cross-sectional area of flow equals the flow rate of the solution.

Additionally and/or alternatively, to reflect flow velocity changes due to both temperature and measured voltage, a calibrated thermometer and temperature-controlled water bath are additionally used. The above calibration curve generation process is repeated for different temperatures (e.g., 35° C. to 39° C.) to form a flow velocity vs. output voltage calibration curve for each temperature. The calibration curves can be combined to form a family of calibration curves. Using a temperature measurement, the appropriate calibration curve can be selected and used to determine a flow velocity based on measured voltage. It has been advantageously discovered that sensor output voltages are approximately linear with temperature. Thus, additional calibration curves can be added to the family of calibration curves using interpolation and/or extrapolation. The calibration curve may then be used by the data logger 106 and/or the data analyzer 108 to estimate, compute, etc. flow velocities based on pairs of measured temperatures and voltages.

While example sensors 501, 502 and example substrates 508 are shown in FIG. 5, one or more of the elements, components, devices, etc. illustrated in FIG. 5 may be combined, divided, re-arranged, omitted, eliminated or implemented in any other way. The sensors 501, 502 and example substrates 508 may include one or more elements, components, devices, etc. in addition to, or instead of, those illustrated in FIG. 5, or may include more than one of any or all of the illustrated elements, components, devices, etc. For example, other patterns, thicknesses, layouts, dimensions, etc. can be used to measure, flow rate, temperature, the portion (e.g., percentage) of the fluid channel 322 that is occluded (e.g., by measuring a conductivity between electrodes of a sensor), a concentration of ions in the urine (e.g., by measuring a conductivity between electrodes of a sensor) or other fluid characteristics (e.g., salinity, pH, sign of infection, blood in urine, etc., and/or a sensitivity, dynamic range, etc. thereof). Further, while hotwire sensors have been discussed by way of an example, other applicable sensors may, additionally and/or alternatively, may be used. For example, ultrasound sensors, optical sensors, mechanical and/or other suitable sensor types may be used.

Figure 6:
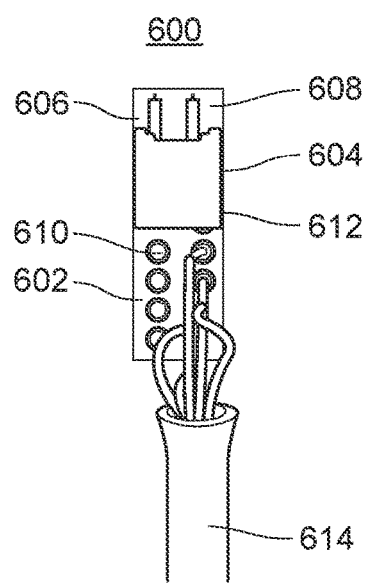
FIG. 6 illustrates an example sensor assembly for the example wearable uroflowmeters disclosed herein.

Turning to FIG. 6, an example sensor assembly 600 that may be used to implement the sensor assembly 336 of FIG. 1 is shown. The sensor assembly 336 includes a printed circuit board (PCB) 602 to which a substrate 604 having one or more sensors 606, 608 (e.g., the substrate 508 having the sensors 501 and 502) is mounted. In some examples, the substrate 604 is structurally coupled to the PCB 602 using an adhesive, and the sensors 606, 608 on the substrate 604 are coupled to respective pads (one of which is designated at reference numeral 610) on the PCB 602 using bonding wires. Bonding wires are encapsulated using an encapsulant 612, such as LOCTITE® Hysol® 1™ encapsulant. A shielded cable 614 with 5 conductors is soldered to the PCB 602. The sensor assembly 600 is assembled into the compartment 340 of the measuring portion 306, and the compartment 340 is sealed using, for example, a silicone sealant. The distance the substrate 604 extends into a fluid channel can be selected to control the sensitivity of the sensors 606, 608.

While a sensor assembly 600 is shown in FIG. 6, one or more of the elements, components, devices, etc. illustrated in FIG. 6 may be combined, divided, re-arranged, omitted, eliminated or implemented in any other way. For example, some or all the analysis performed by the data logger 106 may be performed by the sensor assembly 600. Further, the sensor assembly 600 may include one or more elements, processes or devices in addition to, or instead of, those illustrated in FIG. 6, or may include more than one of any or all of the illustrated elements, components, devices, etc.

Referring now to FIG. 8, a block diagram of an example computing system 800 that may be used to implement all or part of the example wearable data logger 106 of FIG. 1 is shown. The computing system 800 includes a processor 802, a program memory 804, a random-access memory (RAM) 806, and a database 816, all of which are interconnected via an address/data bus 808. The program memory 804 may store software, and machine- or computer-readable instructions, which may be executed by the processor 802.

It should be appreciated that although FIG. 8 depicts only one processor 802, the computing system 800 may include multiple processors 802. The processor 802 of the illustrated example is hardware, and may be a semiconductor based (e.g., silicon based) device. Example processors 802 include a microcontroller, a programmable processor, a programmable controller, a graphics processing unit (GPU), a digital signal processor (DSP), an application specific integrated circuit (ASIC), a programmable logic device (PLD), an field programmable gate array (FPGA), a field programmable logic device (FPLD), etc.

The program memory 804 may include volatile and/or non-volatile memories, for example, one or more RAMs (e.g., a RAM 810) or one or more program memories (e.g., a read-only memory (ROM) 812), or a cache (not shown) storing one or more corresponding software, and machine- or computer-readable instructions. For example, the program memory 804 stores software, and machine- or computer-readable instructions, or computer-executable instructions that may be executed by the processor 802 to perform the example method of FIG. 9. Modules, systems, etc. instead of and/or in addition to those shown in FIG. 8 may be implemented. The software, machine-readable instructions, or computer-executable instructions may be stored on separate non-transitory computer- or machine-readable storage mediums or disks, or at different physical locations.

Example memories 804, 810, 812 include any number or type(s) of volatile or non-volatile non-transitory computer- or machine-readable storage medium or disk, such as a semiconductor memories, magnetically readable memories, optically readable memories, hard disk drive (HDD), an optical storage drive, a solid-state storage device, a solid-state drive (SSD), a ROM, a RAM, a compact disc (CD), a compact disc read-only memory (CD-ROM), a digital versatile disk (DVD), a Blu-ray disk, a redundant array of independent disks (RAID) system, a cache, a flash memory, or any other storage device or storage disk in which information may be stored for any duration (e.g., permanently, for an extended time period, for a brief instance, for temporarily buffering, for caching of the information, etc.).

As used herein, the term non-transitory computer-readable medium is expressly defined to include any type of computer-readable storage device and/or storage disk and to exclude propagating signals and to exclude transmission media. As used herein, the term non-transitory machine-readable medium is expressly defined to include any type of machine-readable storage device and/or storage disk and to exclude propagating signals and to exclude transmission media.

The processor 802 stores sensor measurement data 814 in non-volatile non-transitory computer- or machine-readable storage medium or disk 812 such as a semiconductor memories, magnetically readable memories, optically readable memories, a HDD, an optical storage drive, a solid-state storage device, an SSD, a ROM, a RAM, a flash memory, or any other storage device or storage disk in which information may be stored for any duration (e.g., permanently, for an extended time period, for a brief instance, for temporarily buffering, for caching of the information, etc.).

The computing system 800 may include any number of different types of peripheral input/output (I/O) circuits or components (one of which is designated at reference numeral 818) that enable the processor 802 to communicate with peripheral I/O devices. The peripheral I/O devices may be any desired type of peripheral I/O device such as a keyboard or buttons 204 (see FIG. 2), a display 206 (see FIG. 2), a navigation device (a mouse, a trackball, a capacitive touch pad, a joystick, etc.), a speaker, a microphone, a printer, a button, a communication interface, an antenna, etc. The display 206 can be used to, for example, display measurements, device status, reset measurement storage, device settings, etc. The buttons 204 can be used to, for example, control the computing system 800, to reset measurement storage, to change settings, etc.

The computing system 800 may include any number or type(s) communication interface circuits (one of which is designated at reference numeral 820) that enable the computing system 800 to communicate with other devices and/or system, such as the wearable uroflowmeter 104 and the data analyzer 108. Example communication interface circuits include an Ethernet interface, a USB interface, a Bluetooth interface, an NFC interface, a Wi-Fi transceiver, etc. Communication interface circuits 820 have associated connectors or ports to receive conductors, antennas, etc., one of which is designated at reference numeral 821.

The computing system 800 may also include any number and/or type(s) of analog circuits, one of which is designated at reference number 822. An example analog circuit 822 includes a controllable DC current source 824 to heat up a sensor to a specific temperature and to change its resistance. A differential amplifier 826 amplifies signals received from a sensor, and outputs of the amplifier 826 power a Wheatstone bridge 828. Midpoints of the Wheatstone bridge 828 are connected to the inputs of the amplifier 826, forming a voltage feedback loop. DC current passing through the sensor filament and consequently its temperature are held generally constant by voltage compensation of the amplifier 826. In one instance, power consumption of the circuit 822 indicates urine flow rate passing over the sensor.

The computing system 800 may include one or more sensors (one of which is designated at reference numeral 832), such as a magnetometer, an accelerometer, a rate gyro sensor, an IMU to measure accelerations, angular rates, and/or orientations in three dimensions, etc.

The computing system 800 may also include a power source 834 to power the computing system 800 and, in some examples, to power a system or device (e.g., the data logger 106) to which the computing system 800 is coupled. Example power sources 834 include a non-rechargeable battery, a rechargeable battery, a wireless power transfer receive, a solar charged battery, etc.

An example implementation of the data logger 106 and the computing system 800 are formed by assembling an Adafruit® Bluefruit nRF52 Feather board with a Nordic nRF52832 BLE module, and an Adafruit Precision NXP 9DoF IMU.

Figure 9:
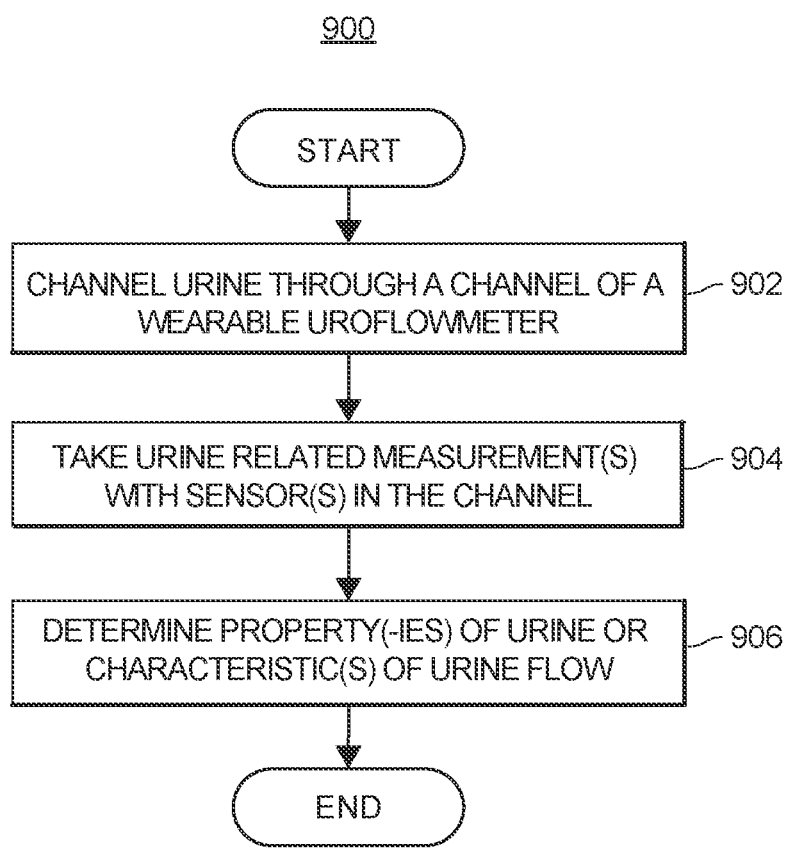
FIG. 9 is a flowchart representative of an example method, hardware logic or machine-readable instructions for the uroflowmetry systems disclosed herein.

A flowchart 900 representative of example hardware logic, machine-readable instructions, hardware implemented state machines, and/or any combination thereof for operating any of the wearable uroflowmeters disclosed herein is shown in FIG. 9. The machine-readable instructions may be an executable program or portion of an executable program for execution by a computer processor such as the processor 802 shown in the example processor platform 800 (discussed above in connection with FIG. 8). The program may be embodied in software stored on a non-transitory computer-readable storage medium such as a CD, a CD-ROM, a floppy disk, a hard drive, a DVD, a Blu-ray disk, or a memory associated with the processor 802, but the entire program and/or parts thereof could alternatively be executed by a device other than the processor 802 and/or embodied in firmware or dedicated hardware. Further, although the example program is described with reference to the flowchart illustrated in FIG. 9, many other methods of operating the disclosed wearable uroflowmeters may alternatively be used. For example, the order of execution of the blocks may be changed, and/or some of the blocks described may be changed, eliminated, or combined. Additionally, and/or alternatively, any or all of the blocks may be implemented by one or more hardware circuits (e.g., discrete and/or integrated analog and/or digital circuitry, an FPGA, an ASIC, a PLD, an FPLD, a comparator, an operational-amplifier (op-amp), a logic circuit, etc.) structured to perform the corresponding operation without executing software or firmware.

The example process of FIG. 9 begins with channeling urine through a channel of a wearable uroflowmeter, as disclosed herein (block 902). Urine can be channeled by, for example, collecting urine with a funnel 314 having a flange 310 to secure the funnel 314 to a person, the collected urine passing from the funnel into a fluid channel 322 where the urine passes over one or more sensors 326 in the channel.

The sensor(s) collect one or more measurement(s) of the urine in the channel (block 904). In some examples, a first sensor operates with a first DC current to take measurements representative of temperature, and a second sensor operates with a second, different DC current to take measurements representative of flow velocity. In some examples, a single sensor operates at different times with the first DC current and the second DC current to take sequential measurements representative of temperature and flow velocity.

Properties of the urine, and/or characteristics of a flow of the urine are determined based on the sensor measurements (block 906). For example, a sensor voltage can be used to determine flow velocity based on a calibration table. Flow velocity can be used, in turn, to determine volume of urine that has passed the sensor in a given period of time as a time integral of a cross-section area of the fluid channel at the sensor multiplied by the instantaneous flow velocities.

Figure 10A:
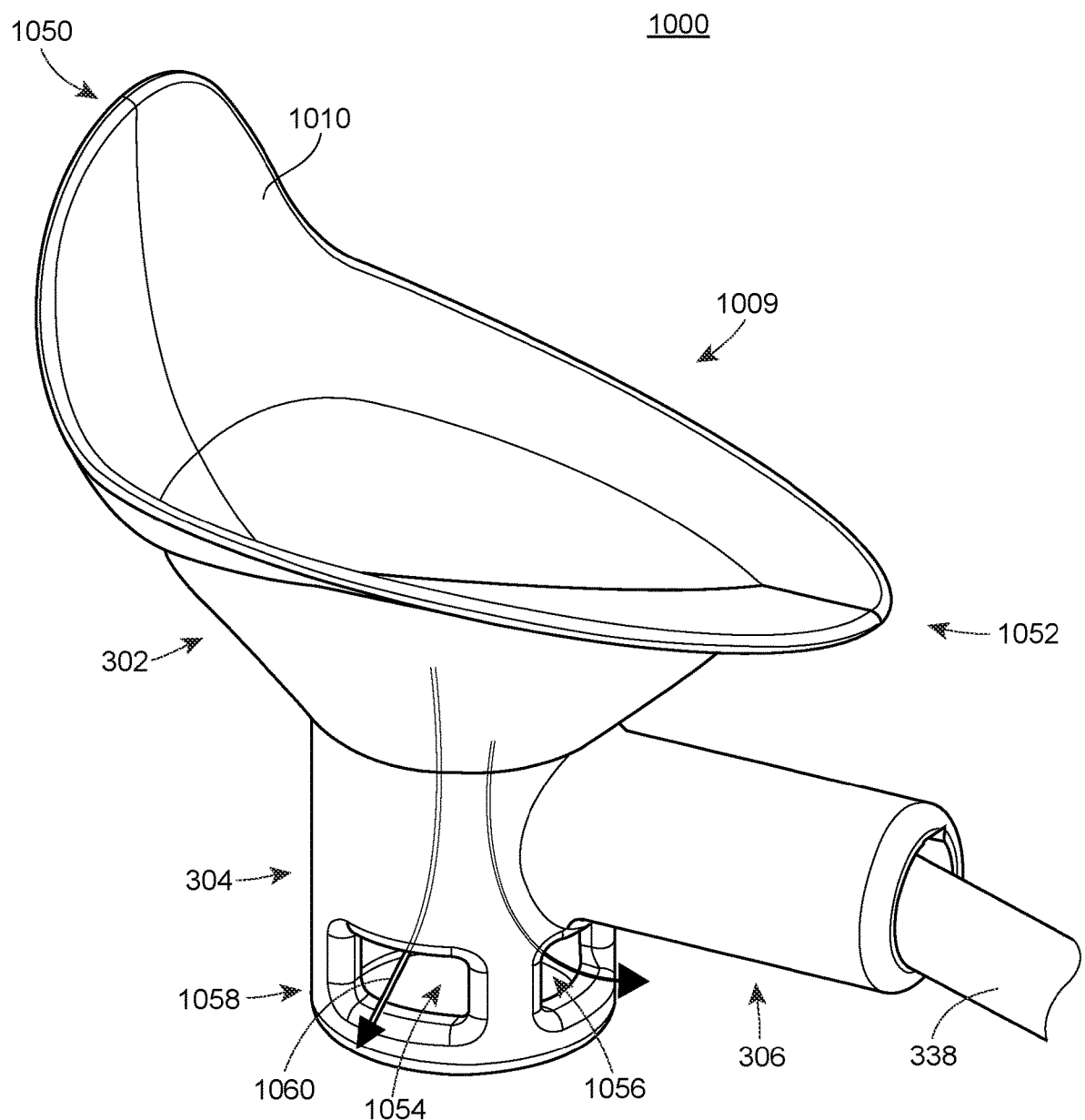
FIG. 10A is a perspective view of another example wearable uroflowmeter for a female that may be used in the example uroflowmetry system of FIGS. 1 and 2.
Figure 10B:
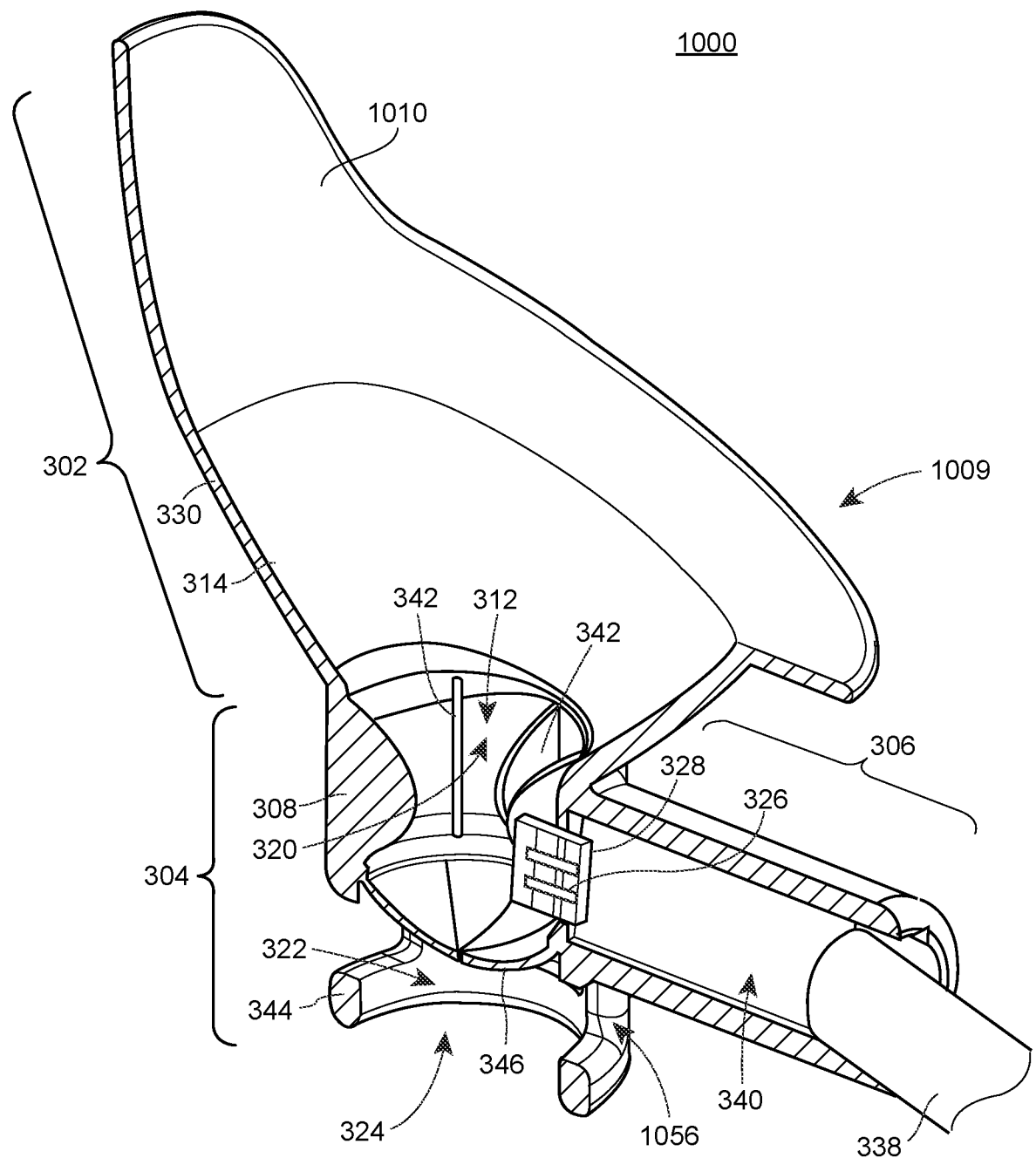
FIG. 10B is an off-axis cross-section view of the example wearable uroflowmeter of FIG. 10A.
Figure 10C:
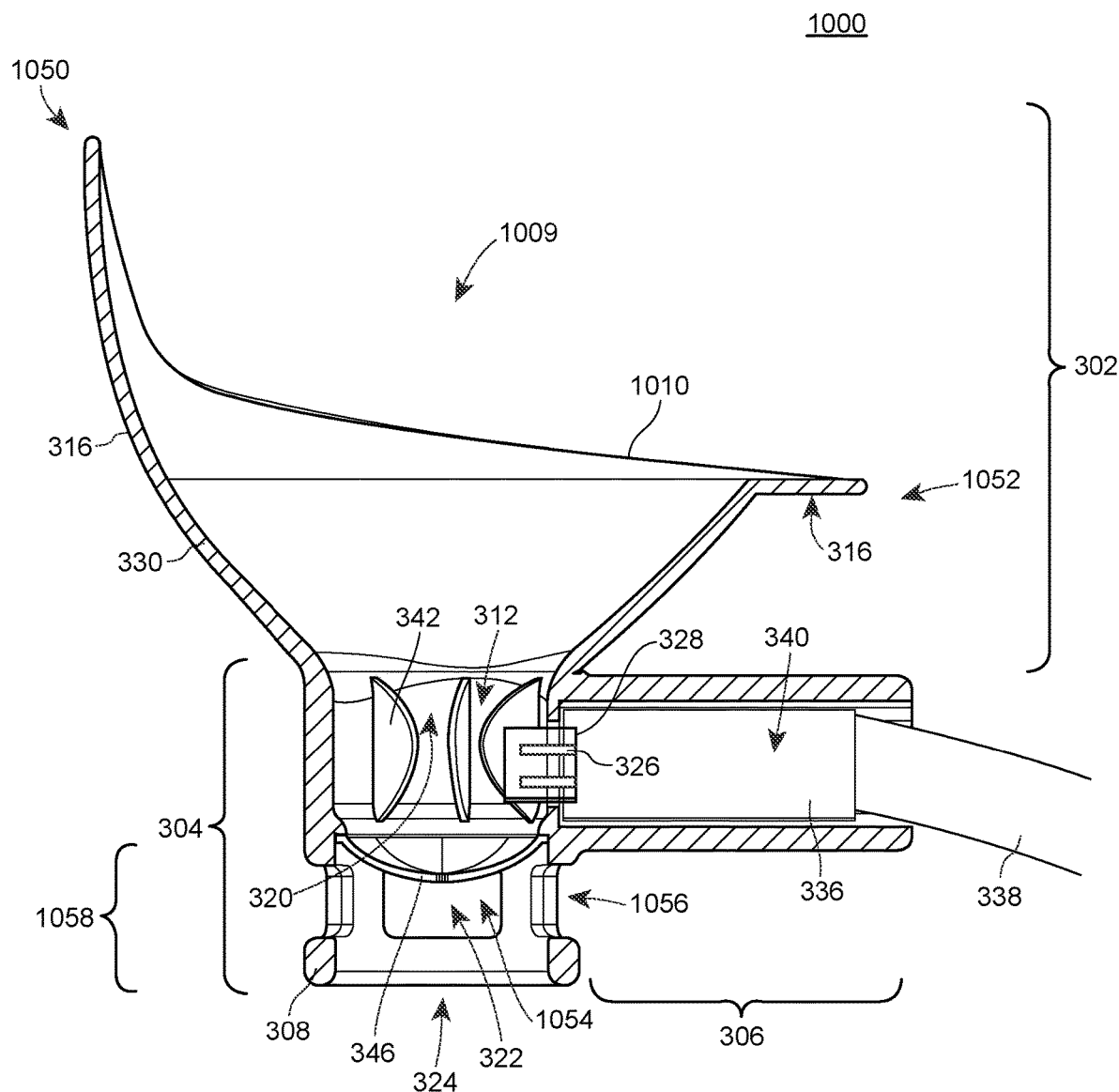
FIG. 10D is a top view of the example wearable uroflowmeter of FIG. 10A.
FIG. 10E is a top off-axis view of the example wearable uroflowmeter of FIG. 10A.
FIG. 10F is a bottom view of the example wearable uroflowmeter of FIG. 10A.
FIG. 10G is a bottom off-axis view of the example wearable uroflowmeter of FIG. 10A.
FIG. 10H is an end view of the example wearable uroflowmeter of FIG. 10A.
Figure 10D:
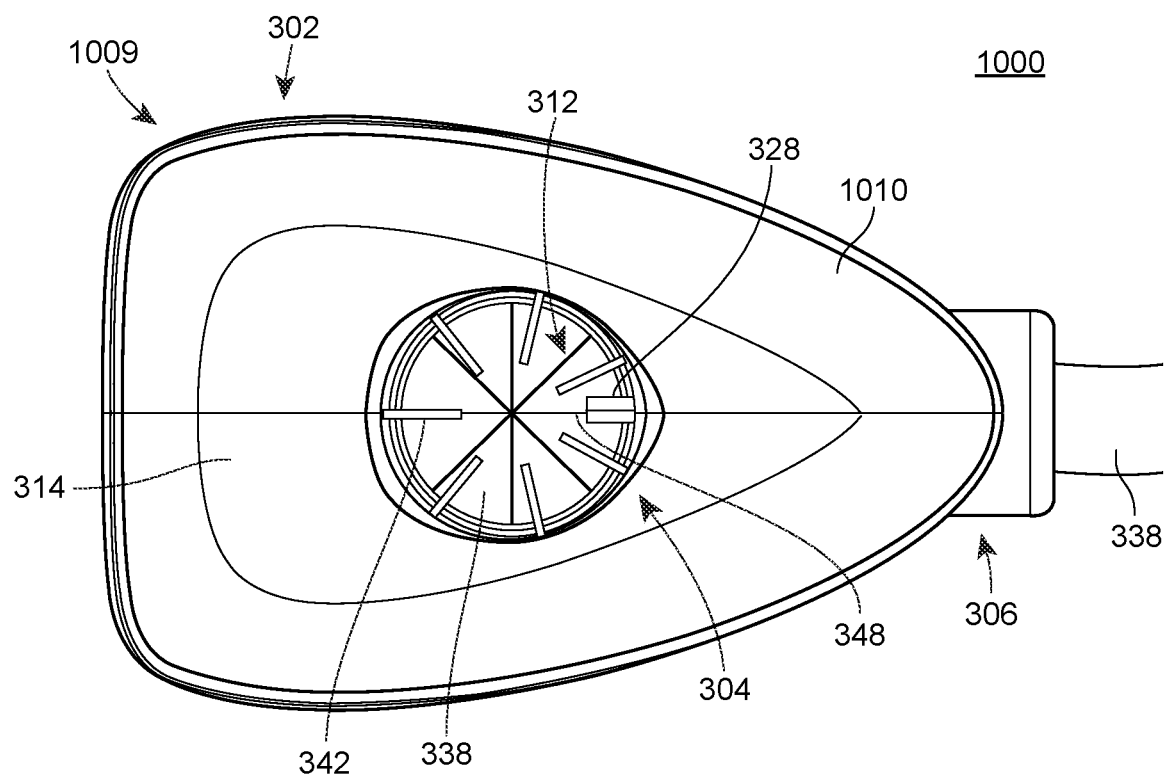
Figure 10E:
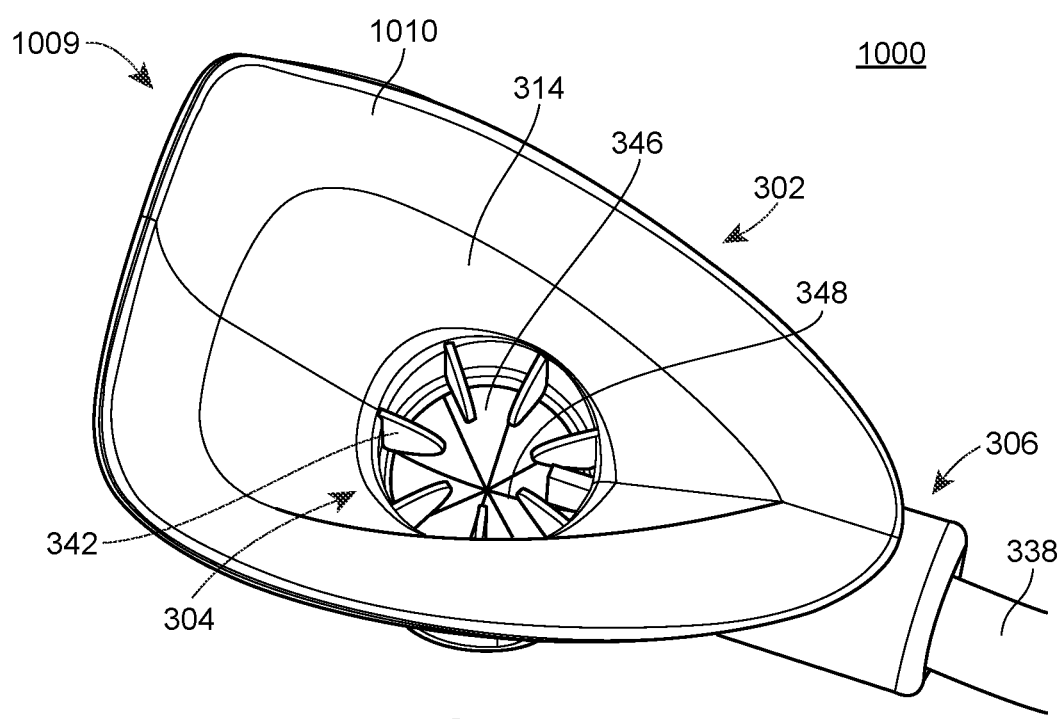
Figure 10F:
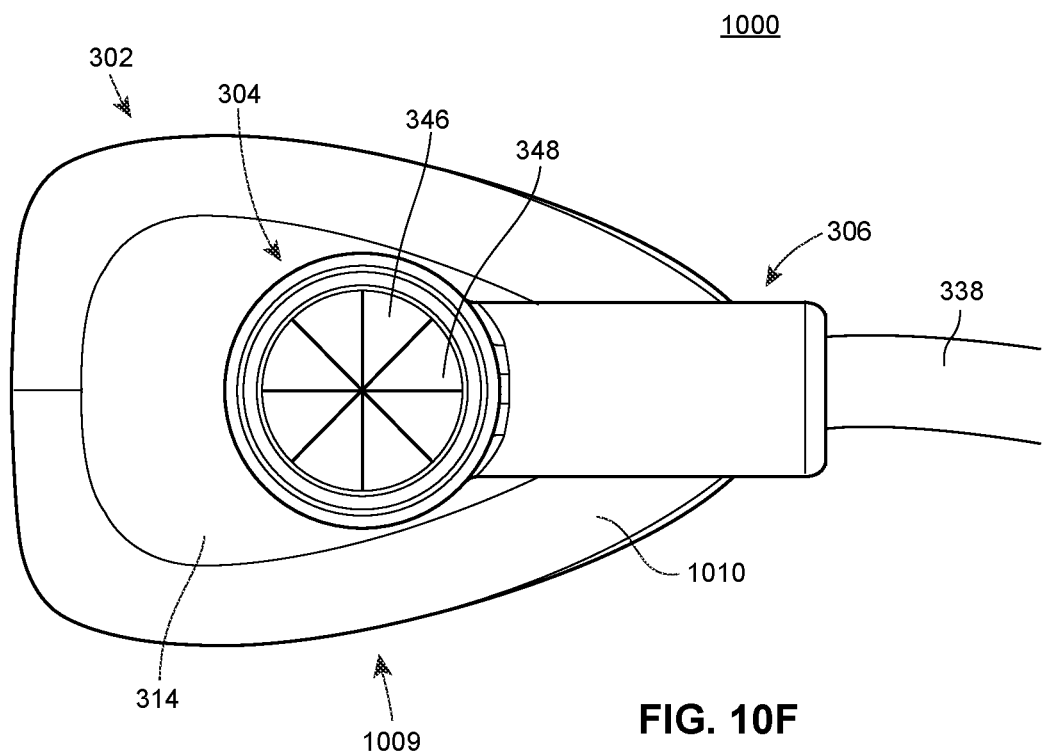
Figure 10G:
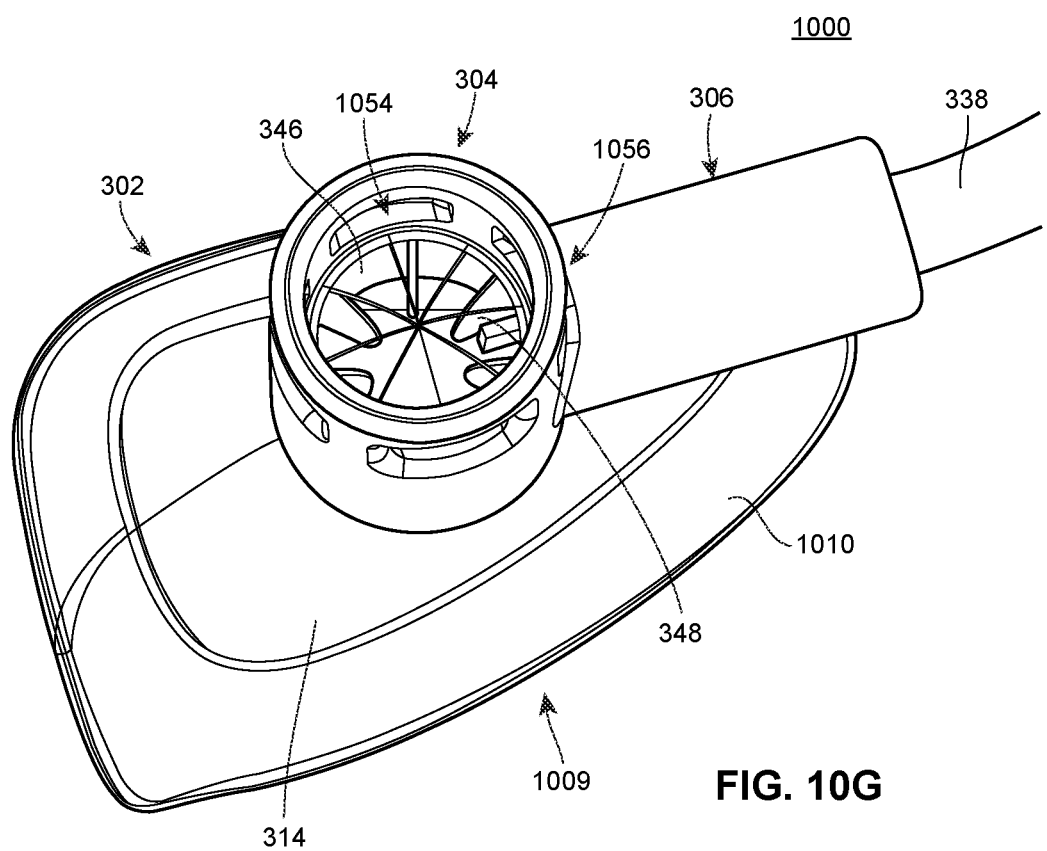
Figure 10H:
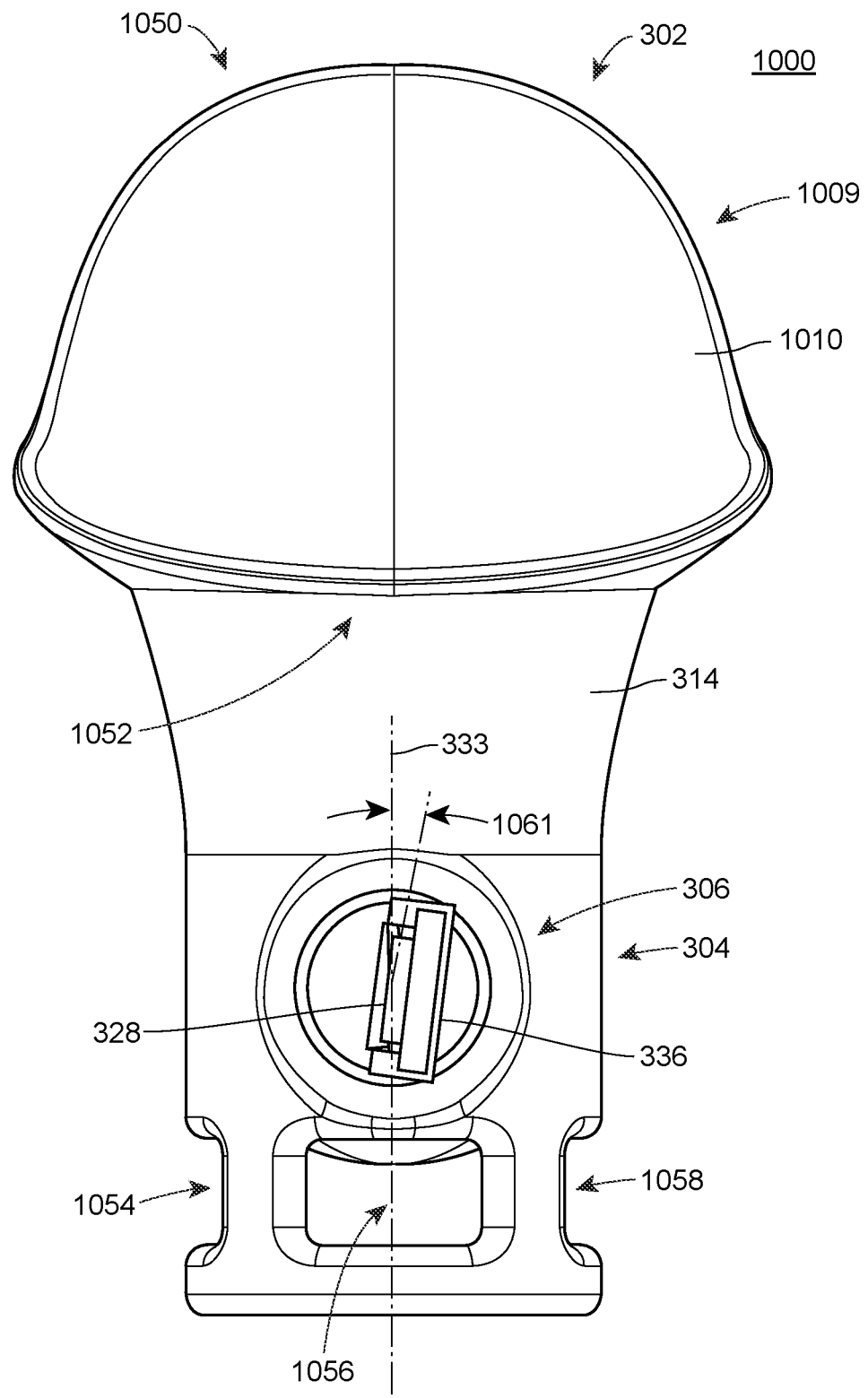

FIG. 10A is a perspective view of another example wearable uroflowmeter 1000 for a female that may be used in the example uroflowmetry system of FIGS. 1 and 2. FIG. 10B is an off-axis cross-section view of the example wearable uroflowmeter 1000 of FIG. 10A. FIG. 100 is a side cross-section view of the example wearable uroflowmeter 1000 of FIG. 10A. FIG. 10D is a top view of the example wearable uroflowmeter 1000 of FIG. 10A. FIG. 10E is a top off-axis view of the example wearable uroflowmeter 1000 of FIG. 10A. FIG. 10F is a bottom view of the example wearable uroflowmeter 1000 of FIG. 10A. FIG. 10G is a bottom off-axis view of the example wearable uroflowmeter 1000 of FIG. 10A. FIG. 10H is an end view of the example wearable uroflowmeter 1000 of FIG. 10A. For clarity of illustration, a reference number may not be shown in all of the FIGS. 10A-10H. Like elements in FIGS. 3A-3D and FIGS. 10A-10H will be designated with the same reference numerals in FIGS. 3A-3D and FIGS. 10A-10H and like elements will not be described again in connection with FIGS. 10A-10H. Instead, the interested reader is referred to the description provided above in connection with FIGS. 3A-3D for a description of the like elements.

The example uroflowmeter 1000 of FIGS. 10A-10H differs from the example uroflowmeter 300 of FIGS. 3A-3D in two aspects. In FIGS. 3A-3D, the end 309 of the funnel portion 302 has an oval shape, and the flange 310 has a planar shape. In contrast, the uroflowmeter 1000 shown in FIGS. 10A-10H an end 1009 of the funnel portion 302 has a sculpted shape 1010 that extends upward at the front 1050 of the uroflowmeter 1000 to prevent urine from splashing out of the uroflowmeter 1000 and is flatter at the back 1052 of the uroflowmeter 1000 for comfort. The sculpted shape may be designed, selected, etc. to conform to the shape of a woman's body.

Additionally or alternatively, the fluid passage portion 304 can includes vents, openings, drains, ports, etc. (two of which are designated at reference numerals 1054 and 1056) in a bottom portion 1058 of the fluid passage portion 304. The ports 1054, 1056 allow urine 1060 to escape from the fluid passage portion 304 when the outlet 324 of the fluid passage portion 304 is partially or wholly occluded by, for example, clothing, absorbent pad, bedding, etc.

The end view of FIG. 10H illustrates an example tilt of the sensor assembly 336 by a small angle 1061 (e.g., 9 degrees) relative to the longitudinal axis 333 of the fluid channel to reduce the formation of eddy currents over the sensors 326 and/or reduce flow separation. The small angle 1061 is selected to be small enough to avoid resistance to urine flow.

Figure 11A:
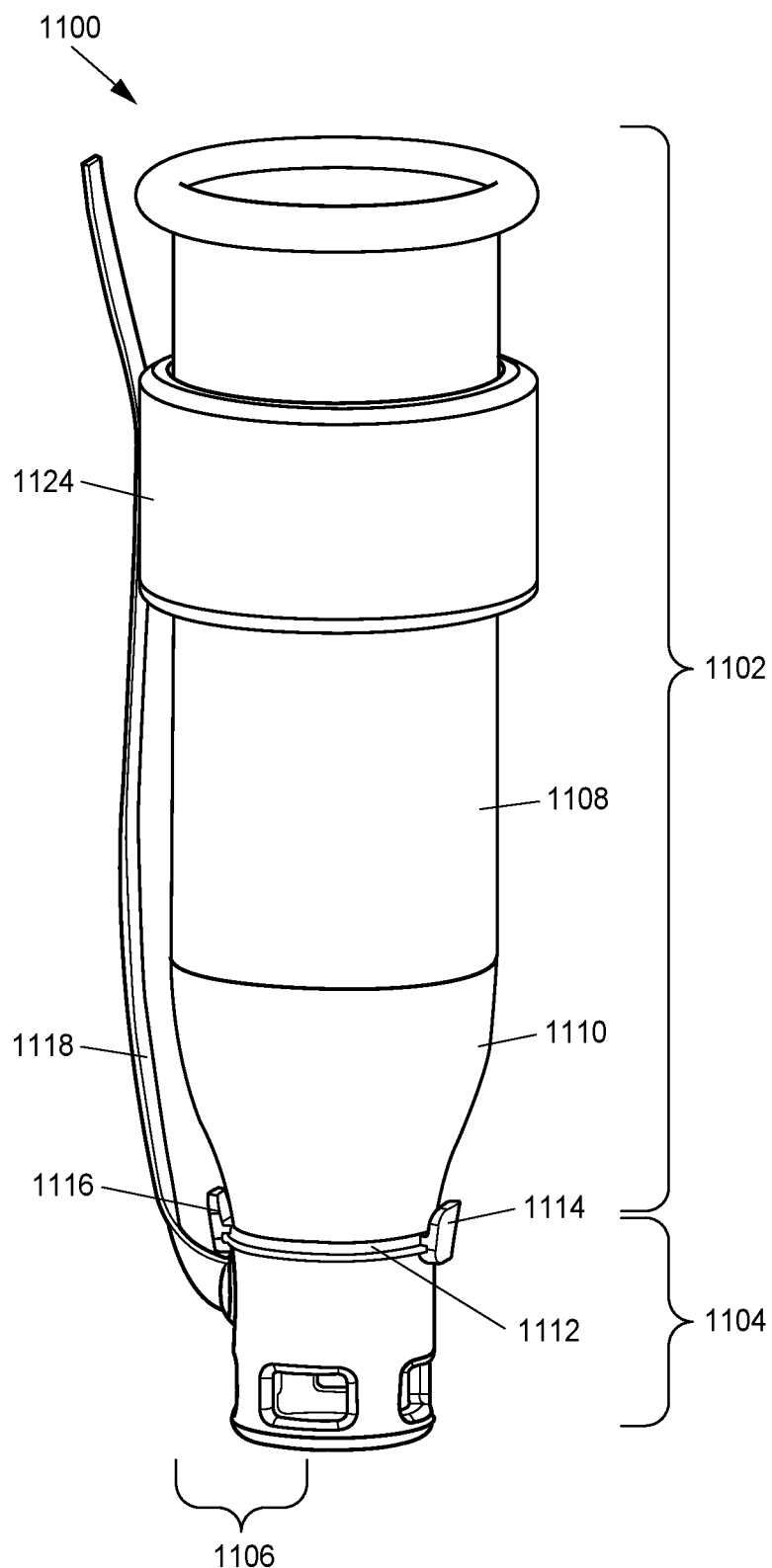
FIG. 11A is a perspective view of an example wearable uroflowmeter for a male that may be used in the example uroflowmetry system of FIGS. 1 and 2.
Figure 11B:
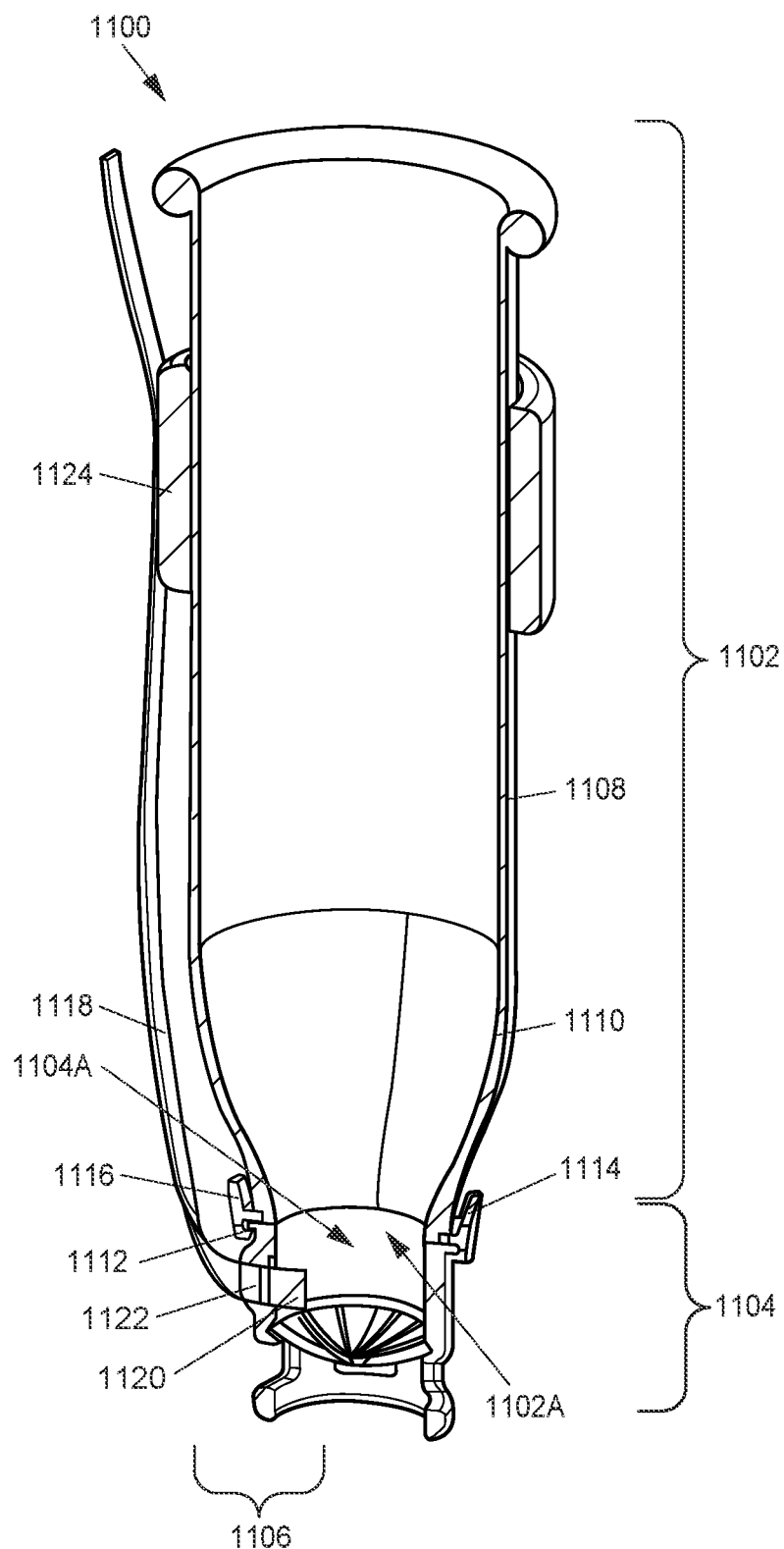
FIG. 11B is an off-axis cross-section view of the example wearable uroflowmeter of FIG. 11A.

FIG. 11A is a perspective view of an example uroflowmeter 1100 for a male that may be used to implement the example wearable uroflowmeter 104 of FIGS. 1 and 2. FIG. 11B is an off-axis cross-section view of the example wearable uroflowmeter 1100.

The example wearable uroflowmeter 1100 includes a funnel portion 1102, a fluid passage portion 1104 and a measuring portion 1106. The example funnel portion 1102 is a flexible, condom-shaped sleeve that preferably conforms to the shape of a penis. The funnel portion 1102 may be formed of an elastic material to minimize any gap between the fluid passage portion 1104 and/or the measuring portion 1106 and the urethral meatus of a penis. During micturition, urine passes from a penis in the funnel portion 1102 through or along the funnel portion 1102 and out of the funnel portion 1102 through an outlet 1102A. The urine passes from the outlet 1102A through an inlet 1104A of the fluid passage portion 1104 into the fluid passage portion 1104.

Figure 12A:
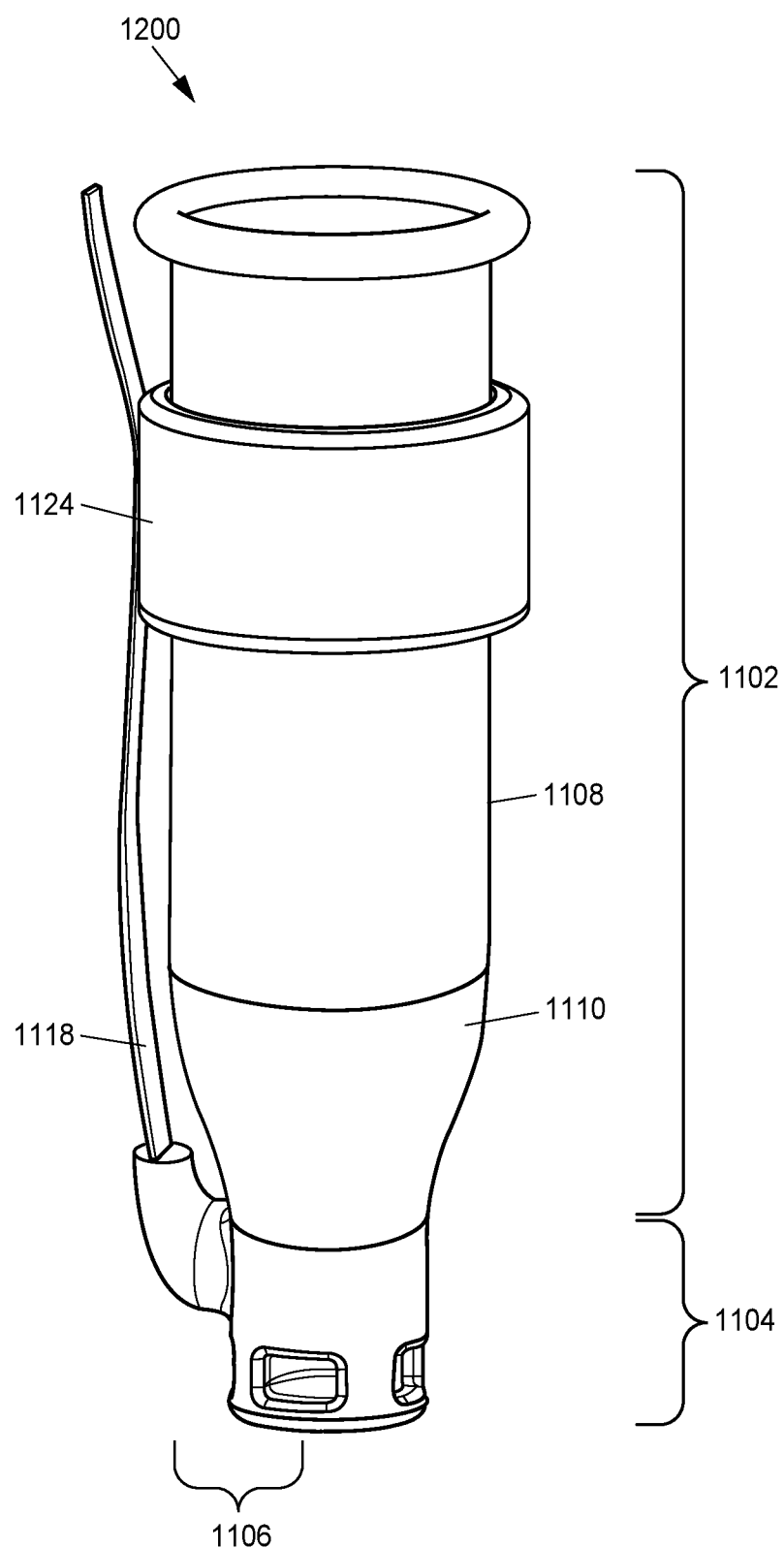
FIG. 12A is a perspective view of another example wearable uroflowmeter for a male that may be used in the example uroflowmetry system of FIGS. 1 and 2.
Figure 12B:
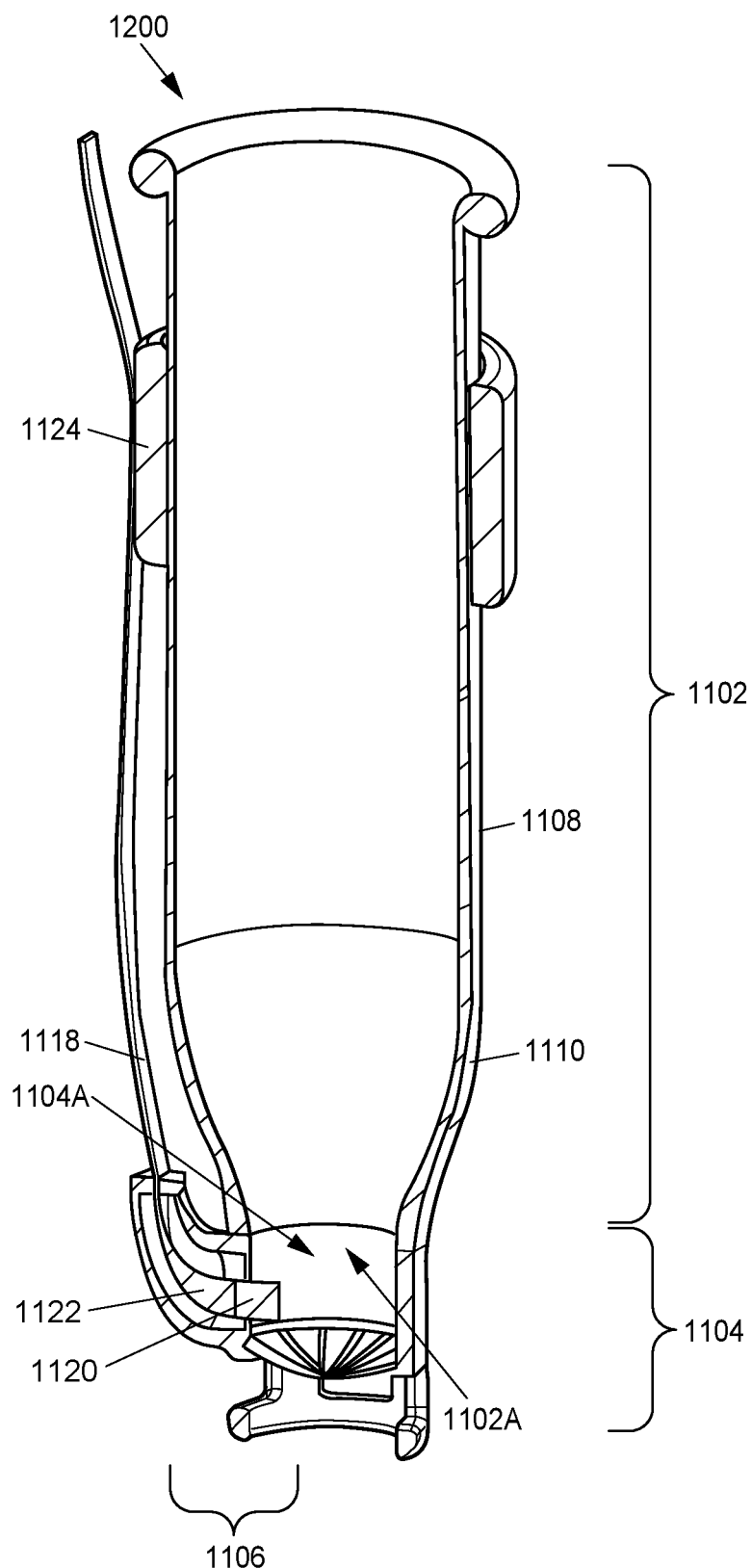
FIG. 12B is an off-axis cross-section view of the example wearable uroflowmeter of FIG. 12A.

The funnel portion 1102 may include two or more segments 1108 and 1110 having different shapes, as shown in FIGS. 11A-11B, 12A-12B and 13A-13B. In some examples, the segment 1110 and/or, more generally, the funnel portion 1102 can pivot, rotate, etc. with respect to the fluid passage portion 1104 so that the fluid passage portion 1104 and the measuring portion 1106 can pivot, rotate, etc. with respect to the penis. Alternatively, the funnel portion 1102 and the fluid passage portion 1104 may be portions of a unitary housing as shown in FIGS. 12A-12B. The segment 1110 may have other features such as internal deformable layers to improve the attachment, comfort and fit of the sleeve to the glans or foreskin of circumcised or uncircumcised individuals.

The male uroflowmeter 1100 of FIGS. 11A-11B may have a modular form that can be assembled upon use and disassembled afterwards for better (re-)usability. For example, in a two-part design, the rigid fluid passage portion 1104 may be attached to the distal end of the funnel portion 1102, after the funnel portion 1102 is worn by the patient. For example, the segment 1110 may include a rigid ring 1112 with one or more snaps 1114, 1116 to secure the funnel portion 1102 to the fluid passage portion 1104. The fluid passage portion 1104 can be detached from the funnel portion 1102 by pressing the snap(s) 1114 and 1116. This configuration advantageously allows free axial rotation of the fluid passage portion 1104 with respect to the funnel portion 1102. Therefore, a cable 1118 carrying sensed information may be passed laterally with respect to the penis to avoid being entangled, stretched or compressed with the movement of the penis shaft. Alternatively, instead of a snap mechanism, one or more magnets may be used to connect and hold the funnel portion 1102 and the fluid passage portion 1104 together. Alternatively, the funnel portion 1102 and the fluid passage portion 1104 may be portions of a unitary housing as shown in FIGS. 12A-12B.

As shown in FIG. 11B, a sensor die 1120 may be directly mounted on a flexible printed circuit board 1122 to transfer signals to the data logger 106 or vice versa, in order to minimize or even eliminate the compartment 340 of the example uroflowmeters of FIGS. 3A-3D and FIGS. 10A-10H. Alternatively, the signals may be passed via flexible conductive paths, e.g., conductive silicone, fibers, ink, or epoxy, over or through the funnel portion 1102 to a superior point or connection on the penis shaft to maximize comfort.

The segment 1108 and/or the funnel portion 1102 may have removable pressure sensitive adhesive (e.g., biocompatible Nusil Med-1353, Med-1356 or Med1-1356) applied to portions of its internal surface. Additionally, the funnel portion 1102 may have an elastic or hook and loop band (e.g., Velcro) 1124 to further secure the funnel portion 1102 to the penis shaft. The band 1124 may also secure the umbilical flexible printed circuit board 1122 to the shaft.

The fluid passage portion 1104 and the measuring portion 1106 may be configured, and operate, substantially similar to the fluid passage portion 304 and the measuring portion 306, respectively, of FIGS. 3A-3D and FIGS. 10A-10H and, thus, description of their operation will not be repeated here. Instead, the interested reader is referred to the description of the fluid passage portion 304 and the measuring portion 306 provided above in connection with FIGS. 3A-3D and FIGS. 10A-10H.

FIG. 12A is a perspective view of another example wearable uroflowmeter 1200 for a male that may be used in the example uroflowmetry system of FIGS. 1 and 2. FIG. 12B is an off-axis cross-section view of the example wearable uroflowmeter 1200. Like (though not necessarily identical) elements in FIGS. 11A-11B and FIGS. 12A-12B are designated with the same reference numerals, and will not be described again in connection with FIGS. 12A-12B. Instead, the interested reader is referred to the description provided above in connection with FIGS. 11A-11B for a description of the like elements.

The example uroflowmeter 1200 of FIGS. 12A-12B differs from the example uroflowmeter 1100 of FIGS. 11A-11B in that the funnel portion 1102 and fluid passageway 1104 are portions of a unitary housing.

Figure 13A:
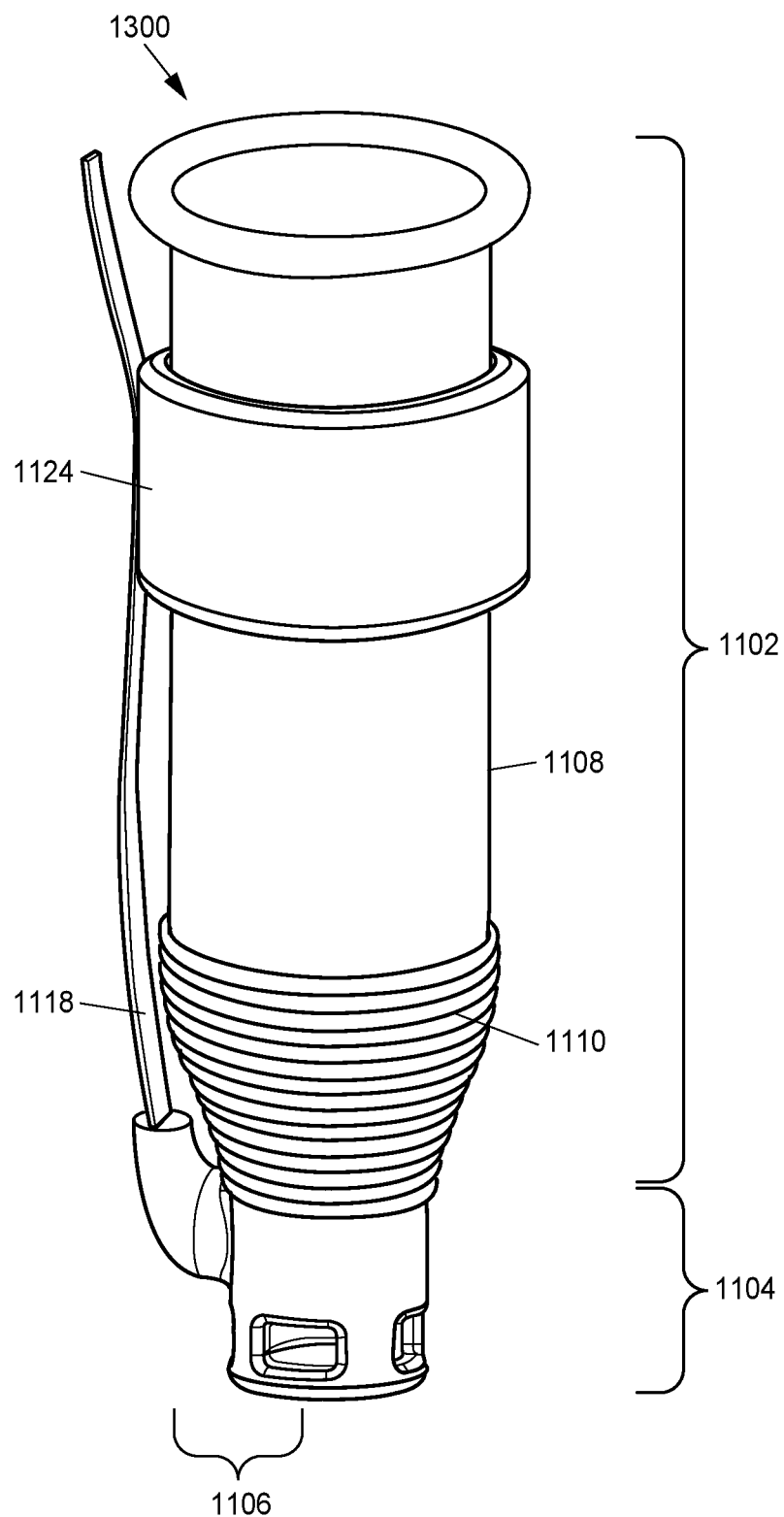
FIG. 13A is a perspective view of yet another example wearable uroflowmeter for a male that may be used in the example uroflowmetry system of FIGS. 1 and 2.
Figure 13B:
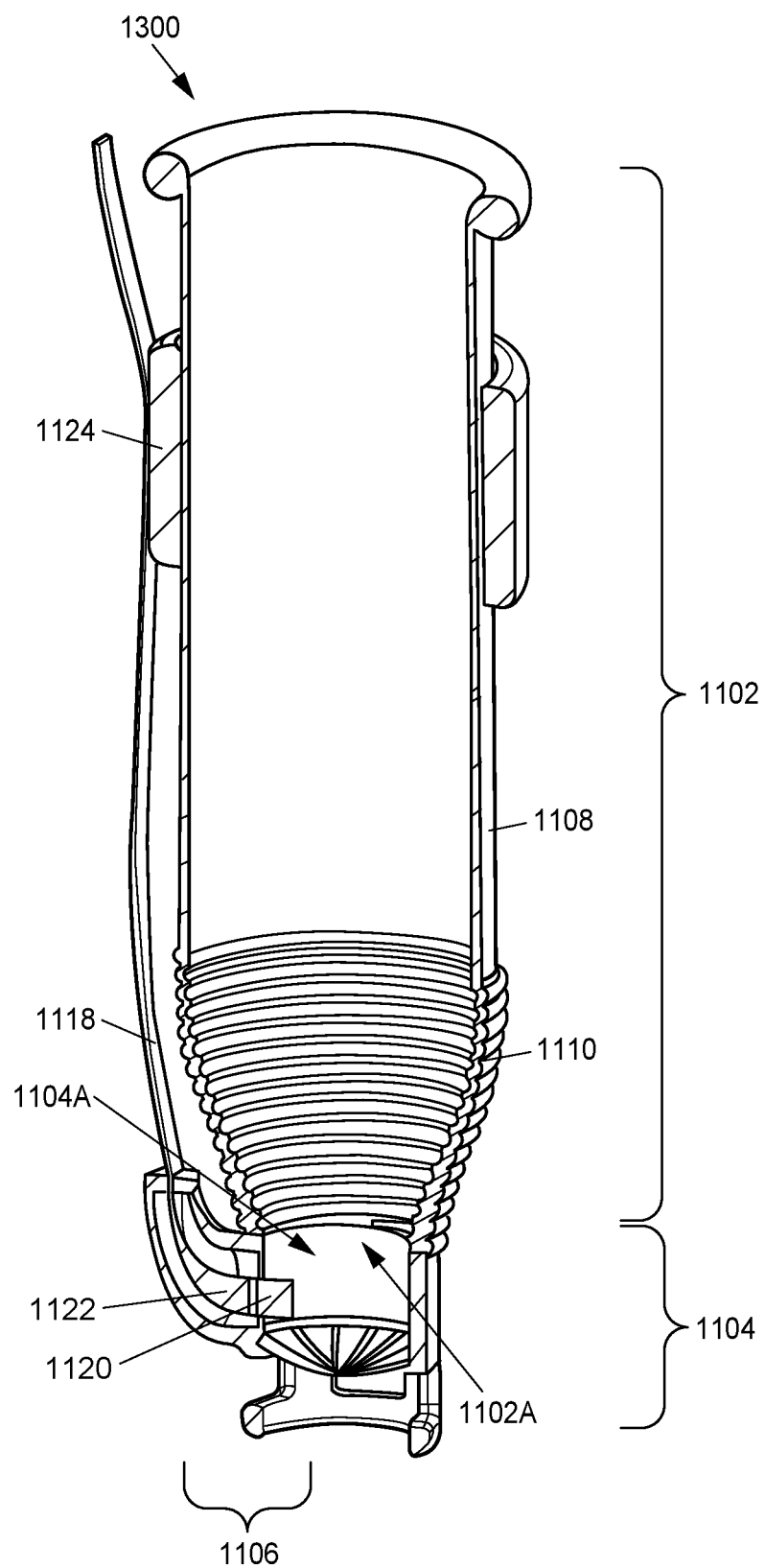
FIG. 13B is an off-axis cross-section view of the example wearable uroflowmeter of FIG. 13A.

FIG. 13A is a perspective view of another example wearable uroflowmeter 1300 for a male that may be used in the example uroflowmetry system of FIGS. 1 and 2. FIG. 13B is an off-axis cross-section view of the example wearable uroflowmeter 1300. Like (though not necessarily identical) elements in FIGS. 11A-11B and FIGS. 13A-13B are designated with the same reference numerals, and will not be described again in connection with FIGS. 13A-13B. Instead, the interested reader is referred to the description provided above in connection with FIGS. 11A-11B for a description of the like elements.

The example uroflowmeter 1300 of FIGS. 13A-13B differs from the example uroflowmeter 1100 of FIGS. 11A-11B in that the funnel portion 1102 and fluid passageway 1104 are portions of a unitary housing, and the segment 1110 is configured with folds, ribs, ridges, a fan-fold, a zigzag shape, an accordion-like shape, or another suitable shape that causes the segment 1110 to be flexible.

Wearable uroflowmetry systems having wearable uroflowmeters, and methods of operating the same are disclosed. Further examples and combinations thereof include at least the following.

Example 1 is a uroflowmetry system, comprising a wearable uroflowmeter including:
- a funnel portion having an end configured to secure the funnel portion against a person, an outlet opposite the end, and a funnel configured to capture urine excreted by the person when the end is secured against the person, and to direct the captured urine into the outlet;
- a fluid passage portion having an opening configured to receive the urine from the outlet of the funnel portion, and a fluid channel to pass the received urine along a length of the fluid passage portion; and
- a measuring portion having a sensor in the fluid channel configured to collect one or more measurements of the urine as the urine passes the sensor, wherein the measurements are representative of at least one of a property of the urine, or a flow characteristic of the urine.

Example 2 is the uroflowmetry system of example 1, wherein the end of the funnel portion includes at least one of an edge, a rim or a flange.

Example 3 is the uroflowmetry system of example 1 or example 2, wherein the fluid passage portion includes one or more shaped structures extending inward from a wall of the fluid channel and oriented longitudinally in the fluid channel such that the urine passes the one or more structures.

Example 4 is the uroflowmetry system of example 3, wherein one of the one or more shaped structures includes a vane.

Example 5 is the uroflowmetry system of any of examples 1 to 4, wherein the fluid passage portion includes one or more ports at a bottom portion of the fluid passage portion.

Example 5B is the uroflowmetry system of any of examples 1 to 5, the fluid passage portion includes a bypass to increase urine flow out of the funnel portion under a high urine flow condition.

Example 6 is the uroflowmetry system of any of examples 1 to 5 and 5B, wherein the fluid passage portion includes a flow restrictor at an outlet of the fluid channel.

Example 7 is the uroflowmetry system of any of examples 1 to 6, wherein the flow restrictor includes a slit flexible membrane having a convex shape.

Example 8 is the uroflowmetry system of example 7, wherein the membrane is located fully or partially inside the fluid channel.

Example 9 is the uroflowmetry system of example 7, wherein the membrane is located fully outside the fluid channel.

Example 10 is the uroflowmetry system of any of examples 1 to 9, wherein the flow restrictor includes at least one of a mesh, an organized fibrous filter, or a randomly organized fibrous filter.

Example 11 is the uroflowmetry system of any of examples 1 to 10, wherein the sensor includes at least one of a hotwire sensor, an ultrasound sensor, or an optical sensor.

Example 12 is the uroflowmetry system of any of examples 1 to 11, wherein the sensor includes at least one of a flow rate sensor, or a temperature sensor.

Example 13 is the uroflowmetry system of any of examples 1 to 12, wherein the sensor is a flow rate sensor, and further comprising a temperature sensor positioned in the fluid channel.

Example 14 is the uroflowmetry system of any of examples 1 to 13, wherein the sensor includes a filament of a planar conductive material formed on a non-conductive substrate according to a geometric pattern.

Example 15 is the uroflowmetry system of example 14, wherein the filament is covered by protective layer.

Example 16 is the uroflowmetry system of example 14 or example 15, wherein the non-conductive substrate includes a glass substrate.

Example 17 is the uroflowmetry system of any of examples 14 to 16, wherein the non-conductive substrate is angled in the fluid channel relative to a longitudinal axis of the fluid channel.

Example 18 is the uroflowmetry system of any of examples 14 to 17, wherein a portion of the filament lies on a surface of the non-conductive substrate.

Example 19 is the uroflowmetry system of any of examples 14 to 18, further comprising a Wheatstone bridge, wherein a voltage difference across the Wheatstone bridge causes an electrical current to flow through the sensor, and wherein the electrical current flowing through the sensor adjusts an electrical resistance of the sensor.

Example 20 is the uroflowmetry system of example 19, wherein a power consumption of the Wheatstone bridge is indicative of a urine flow velocity at the sensor.

Example 21 is the uroflowmetry system of any of examples 1 to 20, wherein the wearable uroflowmeter further includes an additional sensor in the fluid channel configured to measure at least one of a salinity of the urine, a pH of the urine, a physical property of the urine, a sign of infection in the urine, blood in urine, cells in the urine, cell derivatives in the urine, proteins in the urine, hormones in the urine, disease-specific biomarkers in the urine, or a chemical property of the urine.

Example 22 is the uroflowmetry system of any of examples 1 to 21, wherein a side wall of the funnel includes an elastic material intended to be responsive to pressure changes in the funnel.

Example 23 is the uroflowmetry system of example 22, further comprising an additional sensor that measures a change in a shape of the funnel.

Example 24 is the uroflowmetry system of example 22 or example 23, wherein a shape of the end is not intended to change in response to normal operating pressure changes.

Example 25 is the uroflowmetry system of any of examples 1 to 24, wherein the end is formed of a first material more flexible than a second material used to form the funnel.

Example 26 is the uroflowmetry system of any of examples 1 to 25, further comprising a data logger configured to collect and store measurements taken by the sensor.

Example 27 is the uroflowmetry system of example 26, further comprising at least one of a magnetometer sensor, an accelerometer sensor, an inertial measurement unit, a global positioning satellite (GPS) receiver, an altimeter sensor, or a rate gyro sensor, wherein the data logger is configured to collect outputs of the at least one of the magnetometer sensor, the accelerometer sensor, the inertial measurement unit, the GPS receiver, the altimeter sensor, or the rate gyro sensor together with outputs of the sensor.

Example 28 is the uroflowmetry system of example 26 or example 27, further comprising at least one of a conductor or a wireless transceiver coupling the sensor to the data logger.

Example 29 is the uroflowmetry system of any of examples 26 to 28, wherein the wearable uroflowmeter includes a housing to convey a portion of a conducting wire including a conductor from the sensor to the data logger, the conductor sealably disposed within the housing.

Example 30 is the uroflowmetry system of any of examples 26 to 29, wherein the data logger further includes:
a housing;
a first interface configured to receive a first conductor coupling the sensor to the data logger;
a second interface configured to couple the data logger to a data analyzer, wherein the second interface is at least one of a port to receive a conductor, or a wireless transceiver;
an analog circuit configured to process measurements taken by the sensor and received via the first interface to determine at least one of the property of the urine, or the flow characteristic of the urine;
a non-volatile memory configured to store the at least one of the property of the urine, or the flow characteristic of the urine;
a first one or more processors configured to control the analog circuit and store the at least one of the property of the urine, or the flow characteristic of the urine in the non-volatile memory;
a display to present one or more of the at least one of the property of the urine, or the flow characteristic of the urine;
a button to control a functionality of the data logger; and
at least one of a battery or a wireless power receiver to power the data logger.

Example 31 is the uroflowmetry system of example 30, further comprising the data analyzer, the data analyzer configured to process at least one of the properties of the urine, or the flow characteristic of the urine to provide diagnostic information to a user by comparing at least one of the properties of the urine, or the flow characteristic of the urine with a pre-programmed pattern.

Example 32 is the uroflowmetry system of example 30 or example 31, wherein the data analyzer is configured to at least one of control or communicate with the data logger via the second interface.

Example 33 is the uroflowmetry system of any of examples 30 to 32, wherein the data analyzer is configured to correlate body orientation and body motion information with at least one of the properties of the urine, or the flow characteristic of the urine to identify specific body motions, body orientations or activities that led to a urine leakage episode.

Example 34 is the uroflowmetry system of example 30, wherein the data analyzer includes:
a communication interface configured to receive the sensor measurements from the data logger;
a second one or more processors configured to analyze the sensor measurements to determine the at least one of the property of the urine, or the flow characteristic of the urine; and
a display configured to present diagnostic information based on at least one of the properties of the urine, or the flow characteristic of the urine.

Example 35 is the uroflowmetry system of any of examples 1 to 34, wherein the end is generally collinear with and proximate to a distal urethral meatus when the end is secured against a body of a female.

Example 36 is the uroflowmetry system of example 35, wherein the funnel portion is configured to be held in place, when the end is secured against the body, by at least one of a suspensory strap, a vacuum, an adhesive, an absorbent dressing or a dry adhesive to form a seal between the body and the end around the distal urethral meatus.

Example 37 is the uroflowmetry system of example 35 or example 36, wherein the end is formed of a pliable material to conform to a shape of at least one of the distal urethral meatus, vestibule, or an adjacent labia.

Example 38 is the uroflowmetry system of example 37, wherein the end conforms without gapping around a perimeter of attachment.

Example 39 is the uroflowmetry system of any of examples 35 to 38, further comprising at least one of a dry adhesive or a vacuum formed between the end and at least one of the distal urethral meatus, or an adjacent labia, to secure the end to the at least one of the urethral meatus, or the adjacent labia.

Example 40 is the uroflowmetry system of example 39, further comprising a vent valve.

Example 41 is the uroflowmetry system of example 1, wherein the end includes an extension to be inserted into a vaginal vestibule when the wearable uroflowmeter is worn.

Example 42 is the uroflowmetry system of example 41, wherein the extension is held in place, when the end is secured against the person, by at least one of an adhesive, a vacuum, an undergarment, an absorbent pad, or a suspensory strap.

Example 43 is the uroflowmetry system of any of examples 1 to 42, wherein the end is generally collinear with and proximate to an external meatus when the funnel portion is secured around a penis of a male.

Example 44 is the uroflowmetry system of example 1 or 43, wherein the funnel portion has a condom shape.

Example 45 is the uroflowmetry system of example 43 or 44, further comprising at least one of an adhesive, a dry adhesive, a vacuum, or a suspensory strap to secure the funnel portion to the penis.

Example 46 is the uroflowmetry system of any of examples 43 to 45, wherein the funnel portion is formed of a pliable material to conform to a shape of the penis.

Example 47 is the uroflowmetry system of any of examples 1 to 46, further comprising a tube configured to drain urine from the fluid passage portion into a pad or a drainage bag.

Example 48 is a method of operating a wearable uroflowmeter, the method comprising:
channeling urine excreted by a person through a funnel portion of a wearable uroflowmeter having an end to secure the funnel portion to the person;
directing the urine channeled in the funnel portion through a fluid channel of the wearable uroflowmeter; and
collecting a measurement of the urine with a sensor in the fluid channel of the wearable uroflowmeter, the measurement representing at least one of a property of the urine, or a characteristic of a flow of the urine during a micturition or urine leakage event.

Example 49 is the method of example 48, further comprising:
passing a first constant electrical current through a first filament of the sensor;
measuring a first voltage across the first filament;
passing a second constant electrical current through a second filament of the sensor, wherein the second constant electrical current is lower than the first constant electrical current;
measuring a second voltage across the second filament; and
determining a temperature of the urine based on the second voltage
determining a first velocity of the urine based on the first voltage and the temperature.

Example 50 is the method of example 49, further comprising:
measuring a third voltage across the first filament for a known temperature and a known flow velocity;
determining a calibration parameter that represents a second flow velocity based on the measured third voltage across the first filament and the known temperature; and
determining the first flow velocity using the calibration parameter based on the determined temperature and the first voltage.

Example 51 is the method of any of examples 48 to 50, further comprising:
passing, during a first period of time, a first constant electrical current through a filament of the sensor;
measuring a first voltage across the filament during the first period of time;
determining a urine flow velocity of the urine based on the first voltage;
passing, during a second period of time, a second constant electrical current through the filament of the sensor, wherein the second constant electrical current is different than the first constant electrical current;
measuring a second voltage across the filament during the second period of time; and
determining a temperature of the urine based on the second voltage.

Example 52 is the method of any of examples 48 to 51, further comprising:
entering a standby mode; and
existing the standby mode based on a presence of urine in the fluid channel.

Example 53 is the method of any of examples 48 to 52, further comprising providing an indication to the person when a urine leakage event occurs.

Example 54 is the method of any of examples 48 to 53, further comprising
determining an instantaneous flow velocity of the urine based on a velocity of the urine and a cross-section area of the fluid channel at the sensor.

Example 55 is the method of any of examples 48 to 54, further comprising:
determining a conductivity between one or more electrodes of the sensor in the fluid channel; and
determining a percentage of the fluid channel that is occluded by the urine based on the conductivity.

Example 56 is the method of any of examples 48 to 55, further comprising determining a concentration of ions in the urine based on a conductivity.

Example 57 is the method of any of examples 48 to 56, further comprising:
sensing a shape of a wall of the funnel with another sensor; and
calculating an instantaneous urine flow velocity of the urine into the funnel and through the fluid channel based on a relationship of pressure to volume for the funnel portion, wherein the relationship of pressure to volume is based on the shape of the wall of the funnel.

Example 58 is the method of any of examples 48 to 57, further comprising calculating a total volume of urine that has passed the sensor in a given period of time includes a product of a time integral of a cross-section area of the fluid channel at the sensor, and an instantaneous urine flow velocity.

Example 59 is the method of any of examples 48 to 58, further comprising:
calculating instantaneous urine flow velocities and/or urine volumes through the fluid channel over a period of time; and
reporting a largest of the instantaneous urine flow velocities and/or urine volumes, and a urine flow velocity and/or urine volume history including the instantaneous urine flow velocities and/or urine volumes.

Example 60 is the method of any of examples 48 to 59, further comprising:
guiding the urine in the fluid channel with one or more shaped structures in the fluid channel;
temporarily retaining urine at an exit of the fluid channel; and
conforming the end to a shape of the person.

Example 61 is the method of any of examples 48 to 60, further comprising:
positioning the wearable uroflowmeter proximate to and generally collinear with a distal urethral meatus; and holding the wearable uroflowmeter in place using at least one of a suspensory strap, a vacuum, an adhesive, or a dry adhesive to form a seal between the person and the end around the distal urethral meatus.

Example 62 is the method of any of examples 48 to 61, further comprising conforming the funnel portion to a penis, the end having a condom shape.

Use of "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise. A device or structure that is "configured" in a certain way is configured in at least that way, but may also be configured in ways that are not listed.

Further, as used herein, the expressions "in communication," "coupled" and "connected," including variations thereof, encompasses direct communication and/or indirect communication through one or more intermediary components, and does not require direct mechanical or physical (e.g., wired) communication and/or constant communication, but rather additionally includes selective communication at periodic intervals, scheduled intervals, aperiodic intervals, and/or one-time events. The embodiments are not limited in this context.

Further still, unless expressly stated to the contrary, "or" refers to an inclusive or and not to an exclusive or. For example, "A, B or C" refers to any combination or subset of A, B, C such as (1) A alone, (2) B alone, (3) C alone, (4) A with B, (5) A with C, (6) B with C, and (7) A with B and with C. As used herein, the phrase "at least one of A and B" is intended to refer to any combination or subset of A and B such as (1) at least one A, (2) at least one B, and (3) at least one A and at least one B. Similarly, the phrase "at least one of A or B" is intended to refer to any combination or subset of A and B such as (1) at least one A, (2) at least one B, and (3) at least one A and at least one B.

Moreover, in the foregoing specification, specific embodiments have been described. However, one of ordinary skill in the art appreciates that various modifications and changes can be made in view of aspects of this disclosure without departing from the scope of the invention as set forth in the claims below. Accordingly, the specification and figures are to be regarded in an illustrative rather than a restrictive sense, and all such modifications made in view of aspects of this disclosure are intended to be included within the scope of present teachings.

Additionally, the benefits, advantages, solutions to problems, and any element(s) that may cause any benefit, advantage, or solution to occur or become more pronounced are not to be construed as a critical, required, or essential features or elements of any or all the claims.

Furthermore, although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

Finally, any references, including, but not limited to, publications, patent applications, and patents cited herein are hereby incorporated in their entirety by reference to the same extent as if each reference were individually and specifically indicated to be incorporated by reference and were set forth in its entirety herein.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A uroflowmetry system, comprising:
    a wearable uroflowmeter including:
        a funnel portion having an end configured to secure the funnel portion against a person, an outlet opposite the end, and a funnel, wherein the funnel is configured to (i) capture urine excreted by the person when the end is secured against the person, and (ii) direct the captured urine into the outlet;
        a fluid passage portion having an opening configured to receive the captured urine from the outlet of the funnel portion, and a fluid channel to pass the received urine along a length of the fluid passage portion, wherein the fluid passage portion includes a plurality of vanes that (i) are arranged radially around a longitudinal axis of the fluid channel, and (ii) extend inward from a wall of the fluid channel, such that the captured urine passes the plurality of vanes; and
        a measuring portion having a sensor in the fluid channel configured to collect one or more measurements of the captured urine as the captured urine passes the sensor, wherein the measurements are representative of at least one of a property of the captured urine, or a flow characteristic of the captured urine.

2. The uroflowmetry system of claim 1, wherein the fluid passage portion includes a flow restrictor at an outlet of the fluid channel, the flow restrictor includes a flexible membrane, and the flexible membrane includes a plurality of slits.

3. The uroflowmetry system of claim 1, wherein the sensor includes a filament of a planar conductive material formed on a planar substrate according to a geometric pattern, and wherein the planar substrate is angled such that the planar substrate is neither parallel nor orthogonal to a longitudinal axis of the fluid channel.

4. The uroflowmetry system of claim 1, wherein a side wall of the funnel includes an elastic material intended to be responsive to pressure changes in the funnel.

5. The uroflowmetry system of claim 4, further comprising an additional sensor that measures a change in a shape of the funnel.

6. The uroflowmetry system of claim 1, further comprising a data logger configured to collect and store measurements taken by the sensor.

7. The uroflowmetry system of claim 6, further comprising at least one of a conductor or a wireless transceiver coupling the sensor to the data logger.

8. The uroflowmetry system of claim 1, wherein the end is collinear with and proximate to a distal urethral meatus when the end is secured against a body of a female.

9. The uroflowmetry system of claim 8, wherein the funnel portion is configured to be held in place, when the end is secured against the body, by at least one of a suspensory strap, a vacuum, an adhesive, an absorbent dressing or a dry adhesive to form a seal between the body and the end around the distal urethral meatus.

10. The uroflowmetry system of claim 8, wherein the end is formed of a pliable material to conform to a shape of at least one of the distal urethral meatus, vestibule, or an adjacent labia.

11. The uroflowmetry system of claim 1, wherein the end includes an extension to be inserted into a vaginal vestibule when the wearable uroflowmeter is worn.

12. The uroflowmetry system of claim 1, wherein the funnel portion has a condom shape.

13. A method of operating a wearable uroflowmeter, the method comprising:
channeling urine excreted by a person through a funnel portion of a wearable uroflowmeter having an end to secure the funnel portion to the person;
directing the urine channeled in the funnel portion through a fluid channel of the wearable uroflowmeter;
guiding the urine in the fluid channel with a plurality of vanes in the fluid channel that (i) are arranged radially around a longitudinal axis of the fluid channel, and (ii) extend inward from a wall of the fluid channel, such that the captured urine passes the plurality of vanes; and
collecting a measurement of the urine with a sensor in the fluid channel of the wearable uroflowmeter, the measurement representing at least one of a property of the urine, or a characteristic of a flow of the urine during a micturition or urine leakage event.

14. The method of claim 13, further comprising:
passing a first constant electrical current through a first filament of the sensor;
measuring a first voltage across the first filament;
passing a second constant electrical current through a second filament of the sensor, wherein the second constant electrical current is lower than the first constant electrical current;
measuring a second voltage across the second filament;
determining a temperature of the urine based on the second voltage; and
determining a first velocity of the urine based on the first voltage and the temperature.

15. The method of claim 13, further comprising:
entering a standby mode; and
exiting the standby mode based on a presence of urine in the fluid channel.

16. The method of claim 13, further comprising determining an instantaneous flow velocity of the urine based on a velocity of the urine and a cross-section area of the fluid channel at the sensor.

17. The method of claim 13, further comprising:
restricting flow at an outlet of the fluid channel using a flexible membrane that includes a plurality of slits.

18. The method of claim 13, wherein collecting the measurement of the urine with the sensor in the fluid channel of the wearable uroflowmeter includes:
collecting the measurement of the urine with a filament of a planar conductive material formed on a planar substrate according to a geometric pattern, the planar substrate being angled such that the planar substrate is neither parallel nor orthogonal to a longitudinal axis of the fluid channel.

19. A method of operating a wearable uroflowmeter, the method comprising:
channeling urine excreted by a person through a funnel portion of a wearable uroflowmeter having an end to secure the funnel portion to the person;
directing the urine channeled in the funnel portion through a fluid channel of the wearable uroflowmeter;
collecting a measurement of the urine with a sensor in the fluid channel of the wearable uroflowmeter, the measurement representing at least one of a property of the urine, or a characteristic of a flow of the urine during a micturition or urine leakage event;
passing a first constant electrical current through a first filament of the sensor;
measuring a first voltage across the first filament;
passing a second constant electrical current through a second filament of the sensor, wherein the second constant electrical current is lower than the first constant electrical current;
measuring a second voltage across the second filament;
determining a temperature of the urine based on the second voltage; and
determining a first velocity of the urine based on the first voltage and the temperature.

* * * * *